US008568331B2

(12) United States Patent
Bertagnoli et al.

(10) Patent No.: US 8,568,331 B2
(45) Date of Patent: Oct. 29, 2013

(54) SYSTEM AND METHODS FOR MONITORING DURING ANTERIOR SURGERY

(75) Inventors: Rudolph Bertagnoli, Straubing (DE); James Gharib, San Diego, CA (US); G. Bryan Cornwall, San Diego, CA (US); Rory Schermerhorn, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 1420 days.

(21) Appl. No.: 11/883,710

(22) PCT Filed: Feb. 2, 2006

(86) PCT No.: PCT/US2006/003967
§ 371 (c)(1),
(2), (4) Date: Jan. 2, 2008

(87) PCT Pub. No.: WO2006/084194
PCT Pub. Date: Aug. 10, 2006

(65) Prior Publication Data
US 2009/0105604 A1    Apr. 23, 2009

Related U.S. Application Data

(60) Provisional application No. 60/649,732, filed on Feb. 2, 2005.

(51) Int. Cl.
*A61B 5/05* (2006.01)
(52) U.S. Cl.
USPC .......................................... 600/554

(58) Field of Classification Search
USPC ................ 600/546, 554, 587, 210; 607/2, 48; 606/32, 170, 207, 83, 84, 90, 86
See application file for complete search history.

(56) References Cited

U.S. PATENT DOCUMENTS

| | | | |
|---|---|---|---|
| 972,983 A | 10/1910 | Arthur | |
| 1,328,624 A | 1/1920 | Graham | |
| 1,548,184 A | 8/1925 | Cameron | |
| 2,704,064 A | 6/1955 | Fizzell et al. | |
| 2,736,002 A | 2/1956 | Oriel | |
| 2,808,826 A | 10/1957 | Reiner et al. | |
| 3,364,929 A | 1/1968 | Ide et al. | |
| 3,664,329 A | 5/1972 | Naylor | |
| 3,682,162 A | 8/1972 | Colyer | |

(Continued)

FOREIGN PATENT DOCUMENTS

| | | |
|---|---|---|
| DE | 299 08 259 | 7/1999 |
| EP | 0 759 307 | 2/1997 |

(Continued)

OTHER PUBLICATIONS

"System and Methods for Monitoring During Anterior Surgery," International Search Report from International Application No. PCT/US2006/003967, Jun. 13, 2007, 2 pages.

(Continued)

*Primary Examiner* — Brian Szmal
(74) *Attorney, Agent, or Firm* — Jonathan Spangler

(57) ABSTRACT

The present invention involves a system and methods for nerve testing during anterior surgery, including but not limited to anterior total disc replacement surgery, nucleus replacement, and interbody fusion.

17 Claims, 22 Drawing Sheets

(56) References Cited

U.S. PATENT DOCUMENTS

| | | | |
|---|---|---|---|
| 3,785,368 | A | 1/1974 | McCarthy et al. |
| 3,830,226 | A | 8/1974 | Staub et al. |
| 3,957,036 | A | 5/1976 | Normann |
| 4,099,519 | A | 7/1978 | Warren |
| 4,164,214 | A | 8/1979 | Stark et al. |
| 4,207,897 | A | 6/1980 | Lloyd et al. |
| 4,224,949 | A | 9/1980 | Scott et al. |
| 4,226,228 | A | 10/1980 | Shin et al. |
| 4,235,242 | A | 11/1980 | Howson et al. |
| 4,285,347 | A | 8/1981 | Hess |
| 4,291,705 | A | 9/1981 | Severinghaus et al. |
| 4,461,300 | A | 7/1984 | Christensen |
| 4,515,168 | A | 5/1985 | Chester et al. |
| 4,519,403 | A | 5/1985 | Dickhudt |
| 4,545,374 | A * | 10/1985 | Jacobson ............ 600/210 |
| 4,561,445 | A | 12/1985 | Berke et al. |
| 4,562,832 | A | 1/1986 | Wilder et al. |
| 4,573,448 | A | 3/1986 | Kambin |
| 4,592,369 | A | 6/1986 | Davis et al. |
| 4,595,018 | A | 6/1986 | Rantala |
| 4,616,660 | A | 10/1986 | Johns |
| 4,633,889 | A | 1/1987 | Talalla |
| 4,658,835 | A | 4/1987 | Pohndorf |
| 4,744,371 | A | 5/1988 | Harris |
| 4,759,377 | A | 7/1988 | Dykstra |
| 4,784,150 | A | 11/1988 | Voorhies et al. |
| 4,807,642 | A | 2/1989 | Brown |
| 4,892,105 | A | 1/1990 | Prass |
| 4,926,865 | A | 5/1990 | Oman |
| 4,962,766 | A | 10/1990 | Herzon |
| 4,964,411 | A | 10/1990 | Johnson et al. |
| 5,007,902 | A | 4/1991 | Witt |
| 5,058,602 | A | 10/1991 | Brody |
| 5,081,990 | A | 1/1992 | Deletis |
| 5,092,344 | A | 3/1992 | Lee |
| 5,125,406 | A | 6/1992 | Goldstone et al. |
| 5,127,403 | A | 7/1992 | Brownlee |
| 5,161,533 | A | 11/1992 | Prass et al. |
| 5,196,015 | A | 3/1993 | Neubardt |
| RE34,390 | E | 9/1993 | Culver |
| 5,255,691 | A | 10/1993 | Otten |
| 5,282,468 | A | 2/1994 | Klepinski |
| 5,284,153 | A | 2/1994 | Raymond et al. |
| 5,284,154 | A | 2/1994 | Raymond et al. |
| 5,299,563 | A | 4/1994 | Seton |
| 5,312,417 | A | 5/1994 | Wilk |
| 5,313,956 | A | 5/1994 | Knutsson et al. |
| 5,313,962 | A | 5/1994 | Obenchain |
| 5,327,902 | A | 7/1994 | Lemmen |
| 5,333,618 | A | 8/1994 | Lekhtman et al. |
| 5,375,067 | A | 12/1994 | Berchin |
| 5,383,876 | A | 1/1995 | Nardella |
| 5,474,558 | A | 12/1995 | Neubardt |
| 5,480,440 | A | 1/1996 | Kambin |
| 5,482,038 | A | 1/1996 | Ruff |
| 5,484,437 | A | 1/1996 | Michelson |
| 5,540,235 | A | 7/1996 | Wilson |
| 5,549,656 | A | 8/1996 | Reiss |
| 5,560,372 | A | 10/1996 | Cory |
| 5,566,678 | A | 10/1996 | Cadwell |
| 5,569,248 | A | 10/1996 | Mathews |
| 5,579,781 | A | 12/1996 | Cooke |
| 5,593,429 | A | 1/1997 | Ruff |
| 5,599,279 | A | 2/1997 | Slotman et al. |
| 5,601,608 | A | 2/1997 | Mouchawar |
| 5,630,813 | A | 5/1997 | Kieturakis |
| 5,671,752 | A | 9/1997 | Sinderby et al. |
| 5,707,359 | A | 1/1998 | Bufalini |
| 5,711,307 | A | 1/1998 | Smits |
| 5,728,046 | A | 3/1998 | Mayer et al. |
| 5,741,253 | A | 4/1998 | Michelson |
| 5,759,159 | A | 6/1998 | Masreliez |
| 5,772,661 | A | 6/1998 | Michelson |
| 5,775,331 | A | 7/1998 | Raymond et al. |
| 5,776,144 | A | 7/1998 | Leysieffer et al. |
| 5,779,642 | A | 7/1998 | Nightengale |
| 5,785,658 | A | 7/1998 | Benaron |
| 5,797,854 | A | 8/1998 | Hedgecock |
| 5,814,073 | A | 9/1998 | Bonutti |
| 5,830,151 | A | 11/1998 | Hadzic et al. |
| 5,851,191 | A | 12/1998 | Gozani |
| 5,853,373 | A | 12/1998 | Griffith et al. |
| 5,860,973 | A | 1/1999 | Michelson |
| 5,862,314 | A | 1/1999 | Jeddeloh |
| 5,872,314 | A | 2/1999 | Clinton |
| 5,885,219 | A | 3/1999 | Nightengale |
| 5,888,196 | A | 3/1999 | Bonutti |
| 5,902,231 | A | 5/1999 | Foley et al. |
| 5,928,139 | A | 7/1999 | Koros et al. |
| 5,928,158 | A | 7/1999 | Aristides |
| 5,976,094 | A | 11/1999 | Gozani et al. |
| 6,004,262 | A | 12/1999 | Putz et al. |
| 6,011,985 | A | 1/2000 | Athan et al. |
| 6,027,456 | A | 2/2000 | Feler et al. |
| 6,038,469 | A | 3/2000 | Karlsson et al. |
| 6,038,477 | A | 3/2000 | Kayyali |
| 6,050,992 | A | 4/2000 | Nichols |
| 6,074,343 | A | 6/2000 | Nathanson et al. |
| 6,104,957 | A | 8/2000 | Alo et al. |
| 6,104,960 | A | 8/2000 | Duysens et al. |
| 6,119,068 | A | 9/2000 | Kannonji |
| 6,120,503 | A | 9/2000 | Michelson |
| 6,126,660 | A | 10/2000 | Dietz |
| 6,128,576 | A | 10/2000 | Nishimoto |
| 6,132,386 | A | 10/2000 | Gozani et al. |
| 6,132,387 | A | 10/2000 | Gozani et al. |
| 6,135,965 | A | 10/2000 | Tumer et al. |
| 6,139,493 | A | 10/2000 | Koros et al. |
| 6,139,545 | A | 10/2000 | Utley |
| 6,146,335 | A | 11/2000 | Gozani |
| 6,161,047 | A | 12/2000 | King et al. |
| 6,181,961 | B1 | 1/2001 | Prass |
| 6,206,826 | B1 | 3/2001 | Mathews et al. |
| 6,224,549 | B1 | 5/2001 | Drongelen |
| 6,259,945 | B1 | 7/2001 | Epstein et al. |
| 6,266,558 | B1 | 7/2001 | Gozani et al. |
| 6,273,905 | B1 | 8/2001 | Streeter |
| 6,292,701 | B1 | 9/2001 | Prass et al. |
| 6,306,100 | B1 | 10/2001 | Prass |
| 6,312,392 | B1 | 11/2001 | Herzon |
| 6,325,764 | B1 | 12/2001 | Griffith et al. |
| 6,334,068 | B1 | 12/2001 | Hacker |
| 6,348,058 | B1 | 2/2002 | Melkent et al. |
| 6,393,325 | B1 | 5/2002 | Mann et al. |
| 6,425,859 | B1 | 7/2002 | Foley et al. |
| 6,425,901 | B1 | 7/2002 | Zhu et al. |
| 6,451,015 | B1 | 9/2002 | Rittman, III et al. |
| 6,466,817 | B1 | 10/2002 | Kaula et al. |
| 6,500,128 | B2 | 12/2002 | Marino |
| 6,507,755 | B1 | 1/2003 | Turner et al. |
| 6,564,078 | B1 | 5/2003 | Marino et al. |
| 6,579,244 | B2 | 6/2003 | Goodwin |
| 6,582,441 | B1 | 6/2003 | He et al. |
| 6,585,638 | B1 | 7/2003 | Yamamoto |
| 6,618,626 | B2 | 9/2003 | West et al. |
| 6,719,692 | B2 | 4/2004 | Kleffner et al. |
| 6,760,616 | B2 | 7/2004 | Hoey et al. |
| 6,770,074 | B2 | 8/2004 | Michelson |
| 6,796,985 | B2 | 9/2004 | Bolger et al. |
| 6,819,956 | B2 | 11/2004 | DiLorenzo |
| 6,847,849 | B2 | 1/2005 | Mamo et al. |
| 6,849,047 | B2 | 2/2005 | Goodwin |
| 6,855,105 | B2 | 2/2005 | Jackson, III et al. |
| 6,902,569 | B2 | 6/2005 | Parmer et al. |
| 6,926,728 | B2 | 8/2005 | Zucherman et al. |
| 6,929,606 | B2 | 8/2005 | Ritland |
| 6,980,921 | B2 | 12/2005 | Anderson et al. |
| 7,050,848 | B2 | 5/2006 | Hoey et al. |
| 7,079,883 | B2 | 7/2006 | Marino et al. |
| 7,089,059 | B1 | 8/2006 | Pless |
| 7,177,677 | B2 | 2/2007 | Kaula et al. |
| 7,207,949 | B2 | 4/2007 | Miles et al. |
| 7,258,688 | B1 | 8/2007 | Shah et al. |
| 7,294,127 | B2 | 11/2007 | Leung et al. |

(56) References Cited

U.S. PATENT DOCUMENTS

| | | |
|---|---|---|
| 7,310,546 B2 | 12/2007 | Prass |
| 2001/0039949 A1 | 11/2001 | Loubser |
| 2001/0056280 A1 | 12/2001 | Underwood et al. |
| 2002/0007129 A1 | 1/2002 | Marino |
| 2002/0072686 A1 | 6/2002 | Hoey et al. |
| 2002/0161415 A1 | 10/2002 | Cohen et al. |
| 2002/0193843 A1 | 12/2002 | Hill et al. |
| 2003/0032966 A1 | 2/2003 | Foley et al. |
| 2003/0078618 A1 | 4/2003 | Fey et al. |
| 2003/0105503 A1 | 6/2003 | Marino |
| 2004/0199084 A1 | 10/2004 | Kelleher et al. |
| 2004/0225228 A1 | 11/2004 | Ferree |
| 2005/0004593 A1 | 1/2005 | Simonson |
| 2005/0004623 A1 | 1/2005 | Miles et al. |
| 2005/0075578 A1 | 4/2005 | Gharib et al. |
| 2005/0080418 A1 | 4/2005 | Simonson et al. |
| 2005/0119660 A1 | 6/2005 | Bourloin |
| 2005/0149035 A1* | 7/2005 | Pimenta et al. ............... 606/86 |
| 2005/0182454 A1* | 8/2005 | Gharib et al. ............... 607/48 |
| 2005/0256582 A1 | 11/2005 | Feree |
| 2006/0025703 A1 | 2/2006 | Miles et al. |
| 2006/0052828 A1 | 3/2006 | Kim et al. |
| 2006/0069315 A1 | 3/2006 | Miles et al. |
| 2006/0224078 A1 | 10/2006 | Hoey et al. |
| 2007/0016097 A1 | 1/2007 | Farquhar et al. |
| 2007/0198062 A1 | 8/2007 | Miles et al. |
| 2007/0293782 A1 | 12/2007 | Marino |
| 2008/0015612 A1 | 1/2008 | Urmey |
| 2008/0039914 A1 | 2/2008 | Cory et al. |
| 2008/0058606 A1 | 3/2008 | Miles et al. |
| 2008/0064976 A1 | 3/2008 | Kelleher et al. |
| 2008/0064977 A1 | 3/2008 | Kelleher et al. |
| 2008/0065178 A1 | 3/2008 | Kelleher et al. |
| 2008/0071191 A1 | 3/2008 | Kelleher et al. |

FOREIGN PATENT DOCUMENTS

| | | |
|---|---|---|
| EP | 0 972 538 | 1/2000 |
| FR | 2 795 624 | 1/2001 |
| FR | 2 796 846 | 2/2001 |
| WO | 00/38574 | 7/2000 |
| WO | 00/66217 | 11/2000 |
| WO | 00/67645 | 11/2000 |
| WO | 01/03604 | 1/2001 |
| WO | 01/37728 | 5/2001 |
| WO | 03/037170 | 5/2003 |
| WO | 2004/012809 | 2/2004 |
| WO | 2005/013805 | 2/2005 |
| WO | 2006/084193 | 8/2006 |

OTHER PUBLICATIONS

"System and Methods for Monitoring During Anterior Surpery," International Preliminary Report on Patentability from International Application No. PCT/US2006/003937, Aug. 7, 2007, 4 pages.

Lenke et al., "Triggered Electromyographic Threshold for Accuracy of Pedicle Screw Placement," Spine, 1995, 20(4): 1585-1591.

"Brackmann II EMG System," Medical Electronics, 1999, 4 pages.

"Neurovision SE Nerve Locator/Monitor", RLN Systems Inc. Operators Manual, 1999, 22 pages.

"The Brackmann II EMG Monitoring System," Medical Electronics Co. Operator's Manual Version 1.1, 1995, 50 pages.

"The Nicolet Viking IV," Nicolet Biomedical Products, 1999, 6 pages.

Anderson et al., "Pedicle screws with high electrical resistance: a potential source of error with stimulus-evoked EMG," Spine, Department of Orthopaedic Surgery University of Virginia, Jul. 15, 2002, 27(14): 1577-1581.

Bose et al., "Neurophysiologic Monitoring of Spinal Nerve Root Function During Instrumented Posterior Lumber Spine Surgery," Spine, 2002, 27(13):1444-1450.

Calancie et al., "Stimulus-Evoked EMG Monitoring During Transpedicular Lumbosacral Spine Instrumentation" Spine, 1994, 19(24): 2780-2786.

Clements et al., "Evoked and Spontaneous Electromyography to Evaluate Lumbosacral Pedicle Screw Placement," Spine, 1996, 21(5): 600-604.

Danesh-Clough et al. ,"The Use of Evoked EMG in Detecting Misplaced Thoracolumbar Pedicle Screws," Spine, Orthopaedic Department Dunedin Hospital, Jun. 15, 2001, 26(12): 1313-1316.

Darden et al., "A Comparison of Impedance and Electromyogram Measurements in Detecting the Presence of Pedicle Wall Breakthrough," Spine, Charlotte Spine Center North Carolina, Jan. 15, 1998, 23(2): 256-262.

Ebraheim et al., "Anatomic Relations Between the Lumbar Pedicle and the Adjacent Neural Structures," Spine, Department of Orthopaedic Surgery Medical College of Ohio, Oct. 15, 1997, 22(20): 2338-2341.

Ford et al. "Electrical Characteristics of Peripheral Nerve Stimulators Implications for Nerve Localization," Regional Anesthesia, 1984, 9: 73-77.

Glassman et al., "A Prospective Analysis of Intraoperative Electromyographic Monitoring of Pedicle Screw Placement With Computed Tomographic Scan Confirmation," Spine, 1995, 20(12): 1375-1379.

Greenblatt et al., "Needle Nerve Stimulator-Locator: Nerve Blocks with a New Instrument for Locating Nerves," Anesthesia& Analgesia, 1962, 41(5): 599-602.

Haig, "Point of view," Spine, 2002, 27(24): 2819.

Haig et al., "The Relation Among Spinal Geometry on MRI, Paraspinal Electromyographic Abnormalities, and Age in Persons Referred for Electrodiagnostic Testing of Low Back Symptoms," Spine, Department of Physical Medicine and Rehabilitation University of Michigan, Sep. 1, 2002, 27(17): 1918-1925.

Holland et al., "Higher Electrical Stimulus Intensities are Required to Activate Chronically Compressed Nerve Roots: Implications for Intraoperative Electromyographic Pedicle Screw Testing," Spine, Department of Neurology, Johns Hopkins University School of Medicine, Jan. 15, 1998, 23(2): 224-227.

Holland, "Intraoperative Electromyography During Thoracolumbar Spinal Surgery," Spine, 1998, 23(17): 1915-1922.

Journee et al., "System for Intra-Operative Monitoring of the Cortical Integrity of the Pedicle During Pedicle Screw Placement in Low-Back Surgery: Design and Clinical Results," Sensory and Neuromuscular Diagnostic Instrumentation and Data Analysis I, 18th Annual International Conference on Engineering in Medicine and Biology Society, Amsterdam, 1996, pp. 144-145.

Maguire et al., "Evaluation of Intrapedicular Screw Position Using Intraoperative Evoked Electromyography," Spine, 1995, 20(9): 1068-1074.

Martin et al. "Initiation of Erection and Semen Release by Rectal Probe Electrostimulation (RPE)," The Journal of Urology, The Williams& Wilkins Co., 1983, 129: 637-642.

Minahan et al., "The Effect of Neuromuscular Blockade on Pedicle Screw Stimulation Thresholds" Spine, Department of Neurology, Johns Hopkins University School of Medicine, Oct. 1, 2000, 25(19): 2526-2530.

Pither et al., "The Use of Peripheral Nerve Stimulators for Regional Anesthesia: Review of Experimental Characteristics Technique and Clinical Applications," Regional Anesthesia, 1985, 10:49-58.

Raj et al., "Infraclavicular Brachial Plexus Block—A New Approach" Anesthesia and Analgesia, 1973, (52)6: 897-904.

Raj et al., "The Use of Peripheral Nerve Stimulators for Regional Anesthesia," Clinical Issues in Regional Anesthesia, 1985, 1(4):1-6.

Raj et al., "Use of the Nerve Stimulator for Peripheral Blocks," Regional Anesthesia, Apr.-Jun. 1980, pp. 14-21.

Raymond et al., "The Nerve Seeker: A System for Automated Nerve Localization," Regional Anesthesia, 1992, 17(3): 151-162.

Shafik, "Cavernous Nerve Simulation through an Extrapelvic Subpubic Approach: Role in Penile Erection," Eur. Urol, 1994, 26: 98-102.

Toleikis et al., "The Usefulness of Electrical Stimulation for Assessing Pedicle Screw Replacements," Journal of Spinal Disorder, 2000, 13(4): 283-289.

Moed et al., "Insertion of an iliosacral implant in an animal model," Journal of Bone and Joint Surgery, Nov. 1999, 81A(11): 1529-1537.

(56) References Cited

OTHER PUBLICATIONS

"NIM-Response, so advanced . . . yet so simple," XoMed, Inc., 1999, 12 pages.

Moed et al., "Intraoperative monitoring with stimulus-evoked electromyography during placement of iliosacral screws," The Journal of Bone and Joint Surgery, Apr. 1998, 81A(4): 10 pages.

"New data analyzer combines the functions of six instruments in one unit" News Release, Nov. 11, 1987, 3 pages.

"NuVasive's spine surgery system cleared in the US," Pharm & Medical Industry Week, Dec. 10, 2001, 1 page.

"Risk Capital Funds," *Innovation*, Mar. 6, 1990, 172: 3 pages.

\* cited by examiner

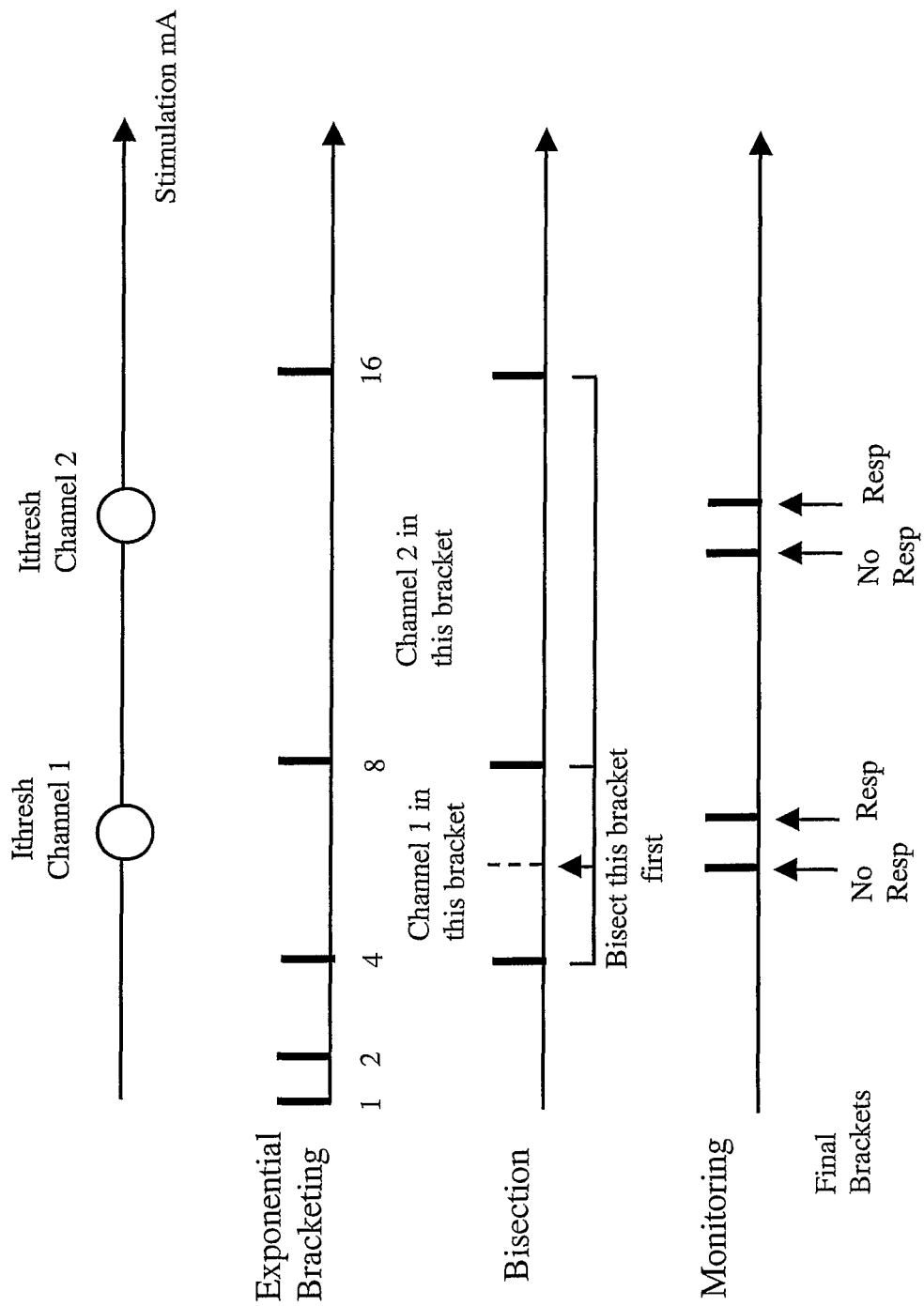

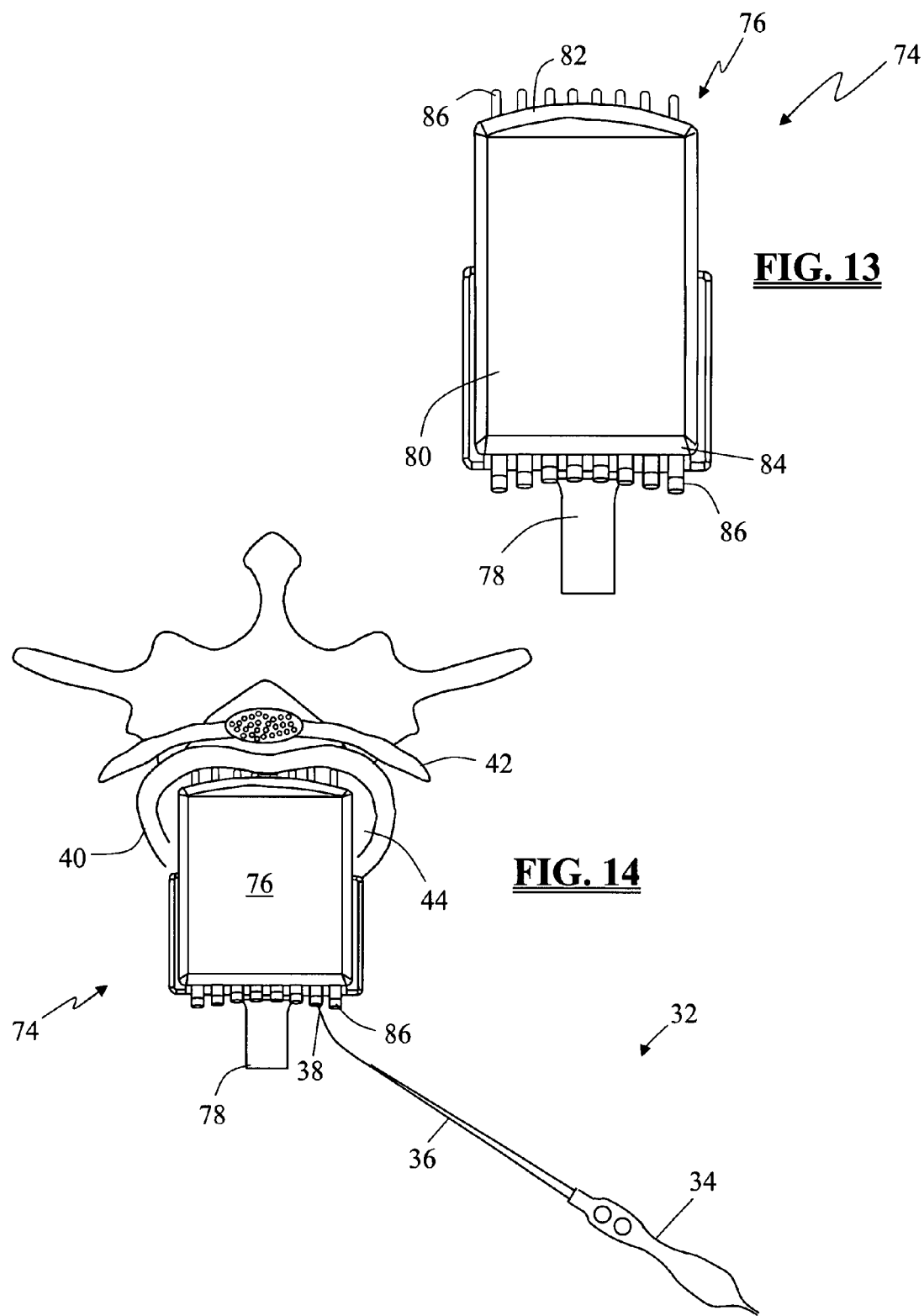

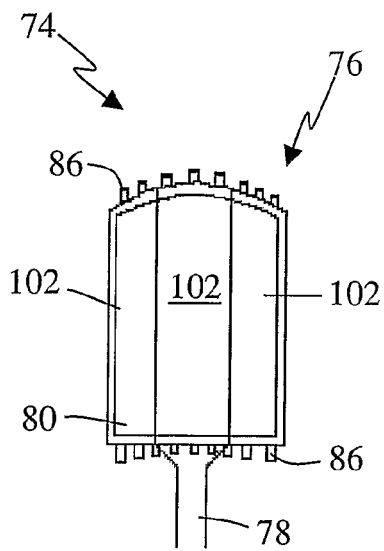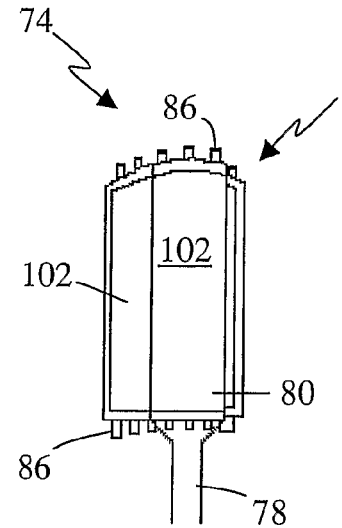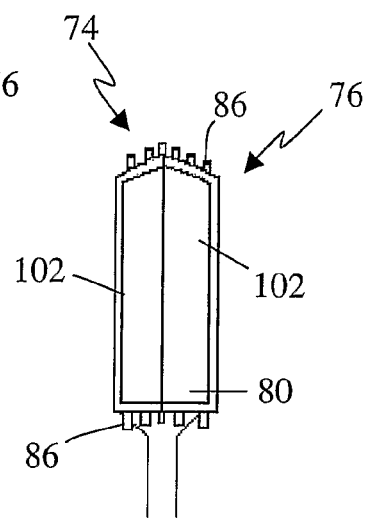
FIG. 26A  FIG. 26B  FIG. 26C
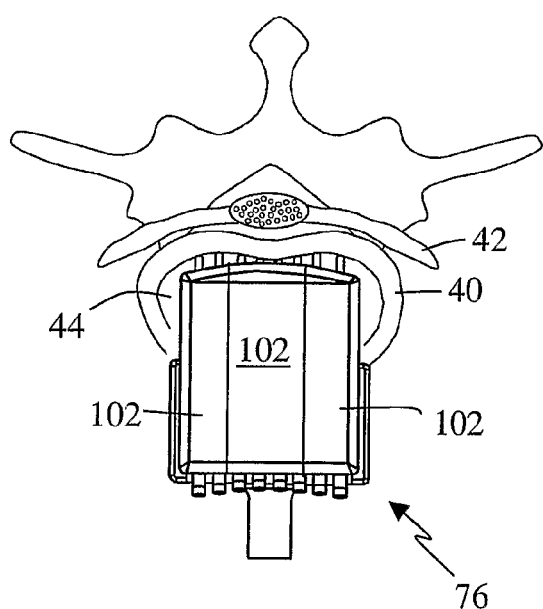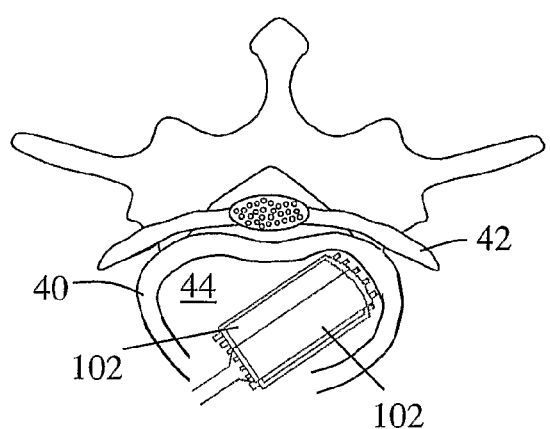
FIG. 27A  FIG. 27B

SYSTEM AND METHODS FOR MONITORING DURING ANTERIOR SURGERY

CROSS REFERENCE TO RELATED APPLICATIONS

The present invention is an International Patent Application and claims the benefit of priority from commonly owned and co-pending U.S. Provisional Patent Application Ser. No. 60/649,732, entitled "System and Methods for Monitoring During Anterior Surgery" and filed on Feb. 2, 2005, the entire contents of which is hereby expressly incorporated by reference into this disclosure as if set forth in its entirety herein. The present application also incorporates by reference the following co-pending and co-assigned patent applications in their entireties: U.S. patent application Ser. No. 10/967,668, entitled "Surgical Access System and Related Methods," filed on Oct. 18, 2004, PCT App. Ser. No. PCT/US2004/025550, entitled "System and Methods for Performing Dynamic Pedicle Integrity Assessments," filed on Aug. 5, 2004.

BACKGROUND OF THE INVENTION

I. Field of the Invention

The present invention relates generally to a system and methods aimed at surgery, and more particularly to system and methods for nerve testing during anterior surgery, including but not limited to anterior disc replacement surgery, nucleus replacement, and interbody fusion.

II. Discussion of the Prior Art

Performing various surgical procedures, including but not necessarily limited to total disc replacement, nucleus replacement, and interbody fusion utilizing an anterior approach provides an advantage over other approaches. Exposing the front of the spine, as opposed to the side or the back, generally allows for a more complete excision of the damaged disc.

Utilizing this advantage however may be complicated. Removing too much of a disc may leave adjacent nerve roots exposed to the danger of surgical tools used in disc preparation or disc implants inadvertently contacting the nerve and resulting in pain or nerve damage to the patient. Thus it is difficult to remove as much of a disc as the surgeon would generally To facilitate the process of disc space preparation and/or implant introduction, it is common to employ a distraction instrument to bias the vertebral bodies on either side of an intervertebral disc away from one another. In so doing, the amount of space between the vertebral bodies is increased, which makes it easier to remove disc material and introduce implants therebetween. One challenge that exits with distracting the vertebral bodies in this manner is that the nerves associated with the particular spinal level can become overstretched during periods of distraction. This may result in neurological impairment (temporary or permanent) for the patient, which can be painful and disruptive to the patient.

Depending upon the type of implant and procedure, a surgeon may elect to compress the vertebral bodies back towards one another after the introduction of the implant. An example would be in a so-called "360 degree" surgery, wherein a fusion implant is introduced into the disc space and a posterior instrumentation system (such as a pedicle screw system) is employed to affix the posterior column of the spine. During such procedures, it is not uncommon to undertake compression of the vertebral bodies towards one another, which can restore spinal alignment and ensure the implant is properly positioned. One challenge that exists with compressing the vertebral bodies together is that the nerves associated with that particular spinal level may become impinged by the vertebral bodies, other boney aspects of the spine, and/or the implants themselves.

The present invention is directed at addressing the above identified challenges.

SUMMARY OF THE INVENTION

The present invention includes systems and related methods for nerve testing during anterior surgery, including assessing the adequacy of disc space preparation as well as monitoring for nerve stretching or compression during vertebral body distraction or intradiscal implant insertion.

According to a broad aspect, the present invention includes a surgical system comprising a control unit and a surgical instrument. The control unit has at least one of computer programming software, firmware and hardware capable of: (a) delivering a stimulation signal, (b) receiving and processing neuromuscular responses due to the stimulation signal, and (c) identifying a relationship between the neuromuscular response and the stimulation signal. The surgical instrument has at least one stimulation electrode electrically coupled to the control unit for transmitting a stimulation signal. The control unit is capable of determining the adequacy of disc space preparation including the relative thickness of the remaining annulus, as well as monitoring for nerve compression and/or stretching.

In a further embodiment of the surgical system of the present invention, the control unit is further equipped to communicate at least one of alphanumeric and graphical information to a user regarding at least one of disc space preparation adequacy and nerve stretching and/or compression.

In a further embodiment of the surgical system of the present invention, the surgical instrument comprises an annulus test probe and the control unit determines the degree of electrical communication between the annulus test probe and adjacent nerves to assess the adequacy of disc space preparation.

In a further embodiment of the surgical system of the present invention, the surgical instrument comprises a disc space probe and the control unit determines the degree of electrical communication between multiple pins of the disc space probe and adjacent nerves to assess the adequacy of disc space preparation.

In a further embodiment of the surgical system of the present invention, the surgical instrument utilizes a position tracking system to determine the position of the annulus test probe or disc space probe within the disc space.

In a further embodiment of the surgical system of the present invention, the surgical instrument is equipped to obtain ultrasound images of the annulus and surrounding tissue.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 9 is a series of graphs illustrating a multi-channel rapid current threshold-hunting algorithm according to one embodiment of the present invention;

FIG. 13 is a top view of the probe member of the disc space probe of FIG. 12;

FIG. 14 is a top cross-sectional view of a prepared disc space with the disc space probe of FIG. 12 inserted;

FIG. 26A-26C Are top views of a forth embodiment of the disc space prove of FIG. 17 where the probe has modular removable sections;

FIGS. 27A-27B are top down views of the disc space probe of FIGS. 26A-26D inserted in a prepared disc space;

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems disclosed herein boast a variety of inventive features and components that warrant patent protection, both individually and in combination.

During an anterior spine surgery, a portion of the disc must be excised from the disc space to make room for the particular implant (e.g. total disc replacement, nucleus replacement, fusion implant). It is generally advantageous to excise as much of a disc as possible, leaving only a thin outer layer of annulus to insulate the adjacent spinal cord and nerves. Breaching or removing too much of the annulus, however, may have unintended consequences, such as allowing inadvertent contact between a disc space preparation tool and/or intradiscal implant and the spinal cord or exiting nerve root. Such contact may potentially result in nerve damage and/or pain for the patient. It is also common during anterior spinal procedures to distract adjacent vertebral bodies in order to access the disc space or restore proper disc height. However, improper (i.e. inadequate or excessive) distraction may also result in nerve damage or pain for the patient. To help avoid these consequences, the present invention is directed at nerve testing during anterior surgery, including but not limited to total disc replacement, nucleus replacement, and interbody fusion surgeries. The invention provides information to help surgeons assess disc space preparation, including but not necessarily limited to, the adequacy of disc removal and the integrity of the remaining annulus, in combination with providing information to help prevent nerve damage during distraction and/or compression of vertebral bodies.

Figure 1:
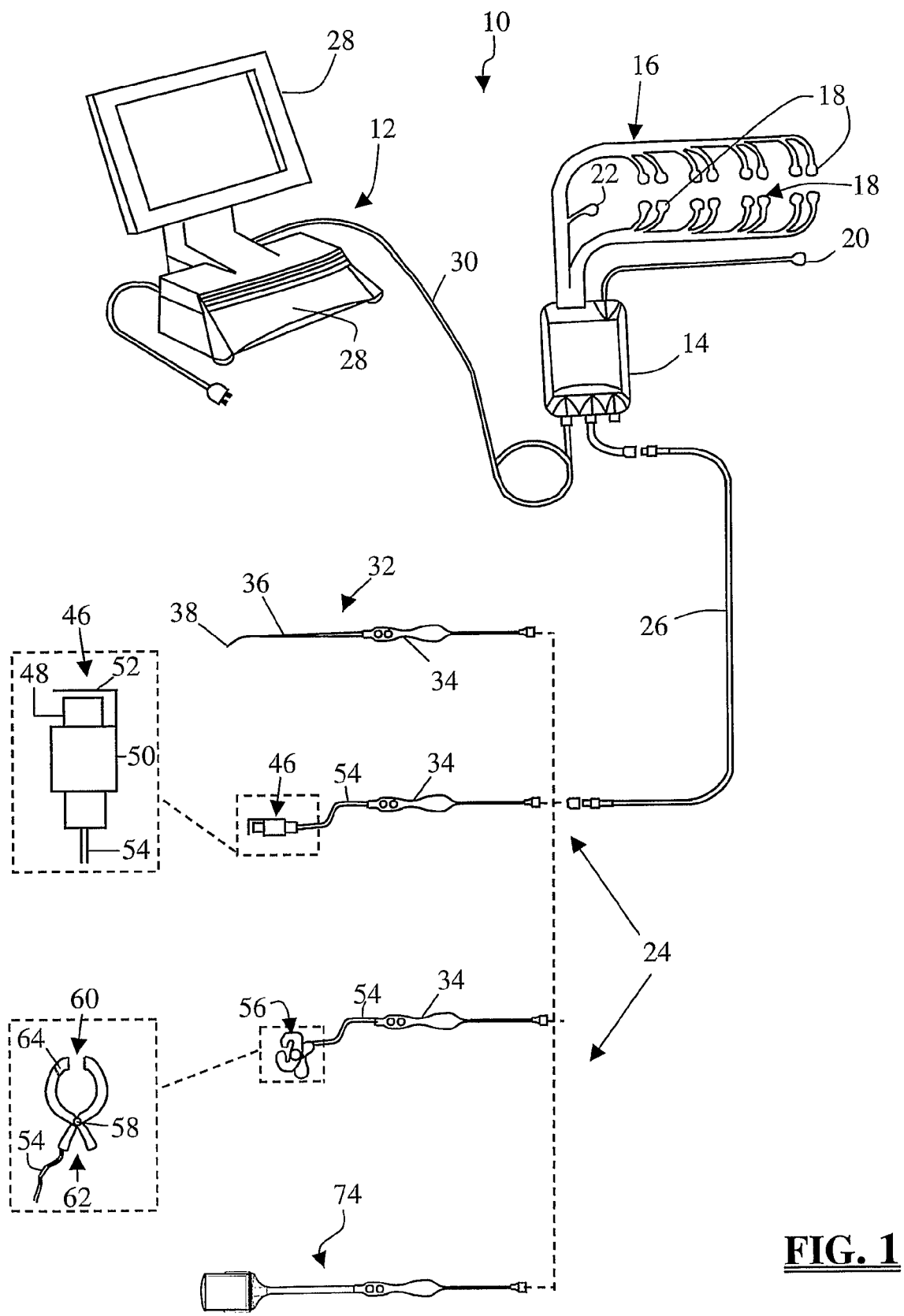
FIG. 1 is a perspective view of an exemplary surgical system 10 capable of nerve testing during anterior surgery (including disc space preparation, nerve stretching and/or nerve compression)
Figure 2:
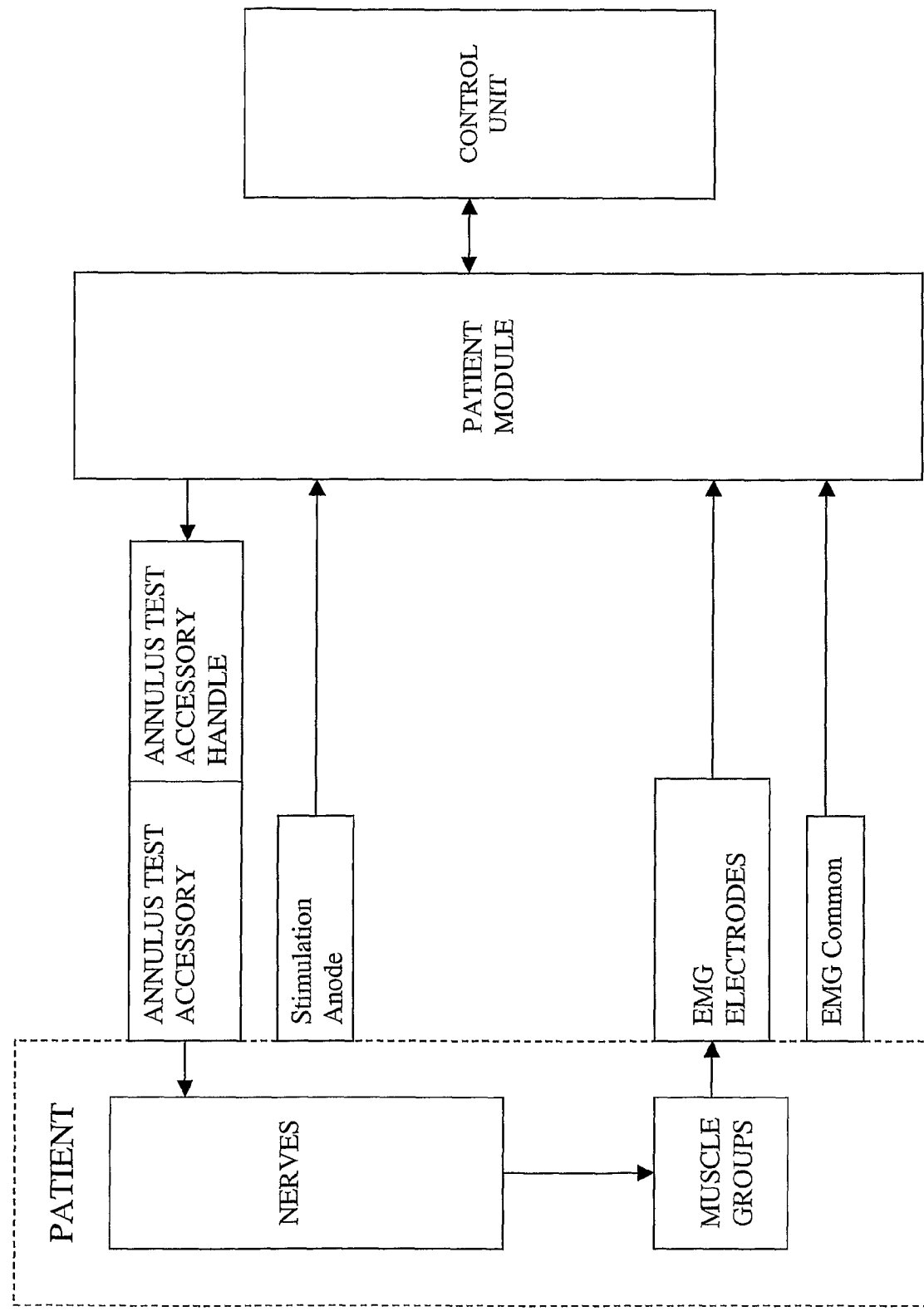
FIG. 2 is a block diagram of the surgical system 10 shown in FIG. 1.

FIG. 1 illustrates, by way of example only, a surgical system 10 capable of carrying out these functions. The surgical system 10 includes a control unit 12, a patient module 14, an EMG harness 16 and return electrode 20 coupled to the patient module 14, and surgical accessories 24 capable of being coupled to the patient module 14 via one or more accessory cables 26. The surgical accessories 24 may include, but are not necessarily limited to, an annulus test probe 32, a disc space probe 70, a plunger-style electrical coupling device 47, and a clip style coupling device 57. With combined reference to the block diagram in FIG. 2, the operation of the surgical system 10 which is readily apparent in view of the following description. The control unit 12 includes a touch screen display 28 and a base 26, which collectively contain the essential processing capabilities for controlling the surgical system 10. The touch screen display 28 is preferably equipped with a graphical user interface (GUI) capable of communicating information to the user and receiving instructions from the user. The base 26 contains computer hardware and software that commands the stimulation sources, receives digitized signals and other information from the patient module 14, processes the EMG responses, and displays the processed data to the operator via the display 28. The primary functions of the software within the control unit 12 include receiving user commands via the touch screen display 28, activating stimulation, processing signal data according to defined algorithms (described below), displaying received parameters and processed data, and monitoring system status.

The patient module 14 is connected via a data cable 30 to the control unit 12, and contains the electrical connections to all electrodes, signal conditioning circuitry, stimulator drive and steering circuitry, and a digital communications interface to the control unit 12. In use, the control unit 12 is situated outside but close to the surgical field (such as on a cart adjacent the operating table) such that the display 28 is directed towards the surgeon for easy visualization. The patient module 14 should be located between the patient's legs, or may be affixed to the end of the operating table at mid-leg level using a bedrail clamp. The position selected should be such that all EMG electrodes can reach their farthest desired location without tension during the surgical procedure.

Figure 4:
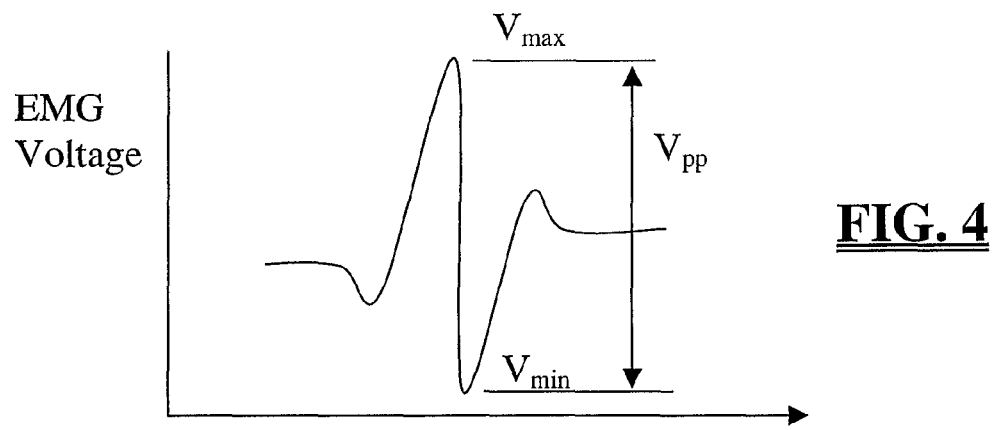
FIG. 4 is a graph illustrating a plot of the neuromuscular response (EMG) of a given myotome over time based on a current stimulation pulse (similar to that shown in FIG. 5) applied to a nerve bundle coupled to the given myotome.
Figure 5:
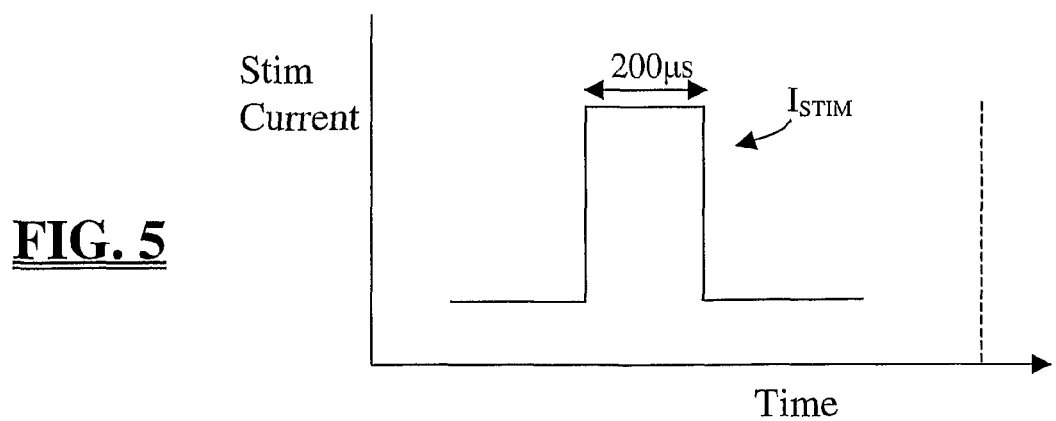
FIG. 5 is a graph illustrating a plot of a stimulation current pulse capable of producing a neuromuscular response (EMG) of the type shown in FIG. 4.

The surgical system 10 conducts nerve testing by electrically stimulating spinal nerves and/or exiting nerve roots lying adjacent to the disc space via one or more stimulation electrodes located on the surgical accessories 24, while monitoring the EMG responses of the muscle groups (myotomes) innervated by the nerves. The evoked responses are then analyzed in relation to the stimulation signal to provide an indication of annular thickness for the given stimulation area. This is best shown in FIG. 4-5, wherein FIG. 4 Illustrates the EMG response of a monitored myotome to the stimulation current pulse shown in FIG. 5. The EMG response can be characterized by a peak-to-peak voltage of $V_{pp}=V_{max}-V_{min}$. The stimulation current may be coupled in any suitable fashion (i.e. AC or DC) and comprises monophasic pulses of 200 μs duration, with an amplitude and frequency that is controlled and adjusted by the software. EMG monitoring may preferably be accomplished by connecting the EMG harness 16 to the myotomes corresponding to the exiting nerve roots associated with the particular spinal operation level. In a preferred embodiment, this is accomplished via 8 pairs of EMG electrodes 18 placed on the skin over the major muscle groups on the legs (four per side), an anode electrode 20 providing a return path for the stimulation current, and a common electrode 22 providing a ground reference to pre-amplifiers in the patient module 14. Although not shown, it will be appreciated that any of a variety of alternative EMG electrodes can be employed, including but not limited to needle electrodes. The EMG responses provide a quantitative measure of the nerve depolarization caused by the electrical stimulus. By way of example, the placement of EMG electrodes 18 may be undertaken according to the manner shown in Table 1 below for spinal surgery:

TABLE 1

| Color | Channel ID | Myotome | Spinal Level |
|---|---|---|---|
| Blue | Right 1 | Right Vastus Medialis | L2, L3, L4 |
| Violet | Right 2 | Right Tibialis Anterior | L4, L5 |
| Grey | Right 3 | Right Biceps Femoris | L5, S1, S2 |
| White | Right 4 | Right Gastroc. Medial | S1, S2 |
| Red | Left 1 | Left Vastus Medialis | L2, L3, L4 |
| Orange | Left 2 | Left Tibialis Anterior | L4, L5 |
| Yellow | Left 3 | Left Biceps Femoris | L5, S1, S2 |
| Green | Left 4 | Left Gastroc. Medial | S1, S2 |

For each nerve and myotome there is a characteristic delay from the stimulation current pulse to the EMG response (typically between 5 to 20 ms). To account for this, the frequency of the current pulses is set at a suitable level such as, in a preferred embodiment, 4 Hz to 10 Hz (and most preferably 4.5 Hz), so as to prevent stimulating the nerve before it has a chance to recover from depolarization.

Figure 6:
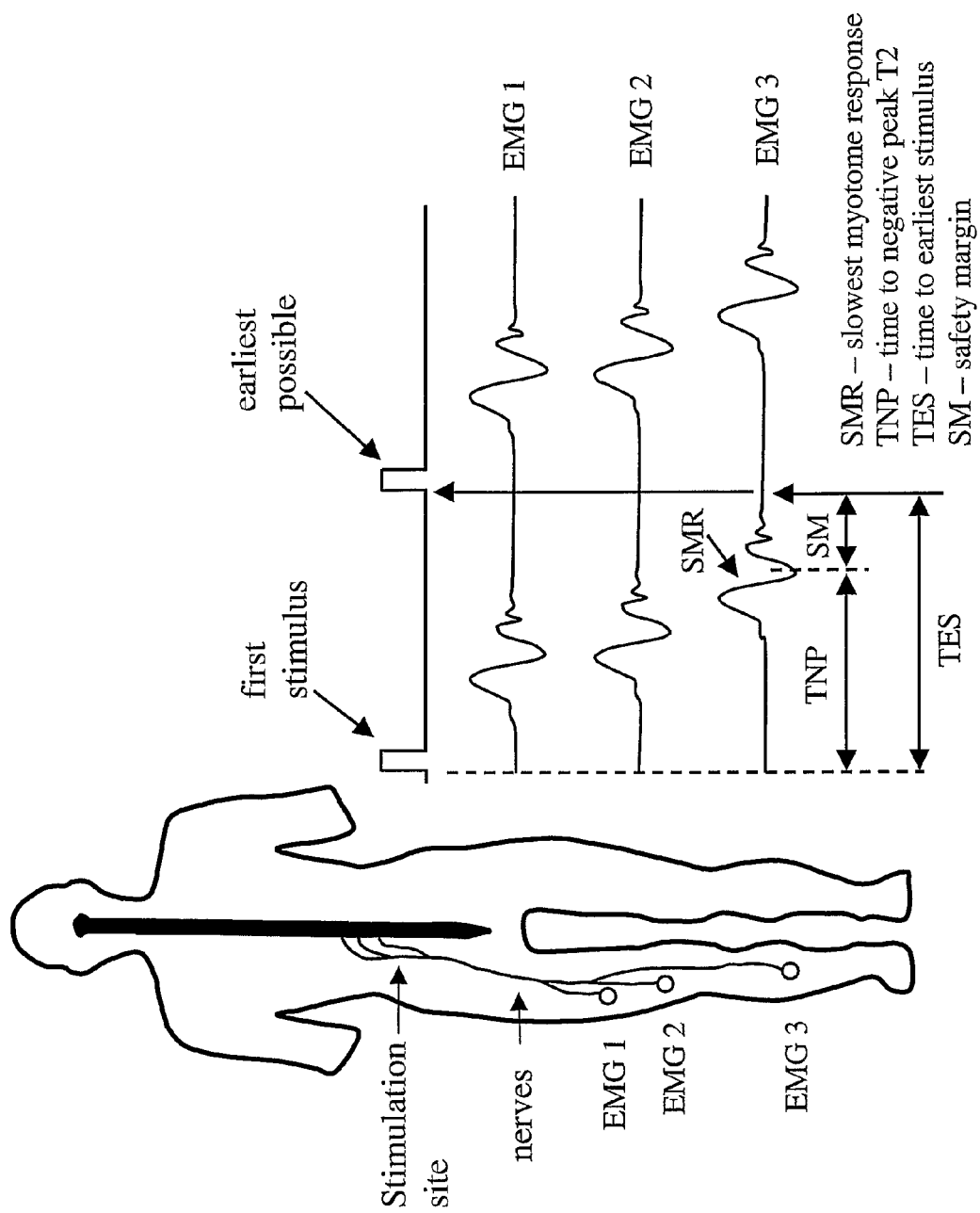
FIG. 6 is an illustration (graphical and schematic) of a method of automatically determining the maximum frequency ($F_{Max}$) of the stimulation current pulses according to one embodiment of the present invention.

FIG. 6 illustrates an alternate manner of setting the maximum stimulation frequency ($F_{max}$), to the extent it is desired to do so rather than simply selecting a fixed maximum stimulation frequency (such as 4.5 Hz) as described above. According to this embodiment, the maximum frequency of the stimulation pulses is automatically adjusted. After each stimulation, $F_{max}$ will be computed as: $F_{max}=1/(T2+T_{Safety\ Margin})$ for the largest value of T2 from each of the active EMG channels. In one embodiment, the Safety Margin is 5 ms, although it is contemplated that this could be varied according to any number of suitable durations. Before the specified number of stimulations, the stimulations will be performed at intervals of 100-120 ms during the bracketing state, intervals of 200-240 ms during the bisection state, and intervals of 400-480 ms during the monitoring state (bracketing, bisection and monitoring states are discussed in detail below). After the specified number of stimulations, the stimulations will be performed at the fastest interval practical (but no faster than $F_{max}$) during the bracketing state, the fastest interval practical (but no faster than $F_{max}/2$) during the bisection state, and the fastest interval practical (but no faster than $F_{max}/4$) during the monitoring state. The maximum frequency used until $F_{max}$ is calculated is preferably 10 Hz, although slower stimulation frequencies may be used during some acquisition algorithms. The value of $F_{max}$ used is periodically updated to ensure that it is still appropriate. For physiological reasons, the maximum frequency for stimulation will be set on a per-patient basis. Readings will be taken from all myotomes and the one with the slowest frequency (highest T2) will be recorded.

Figure 7:
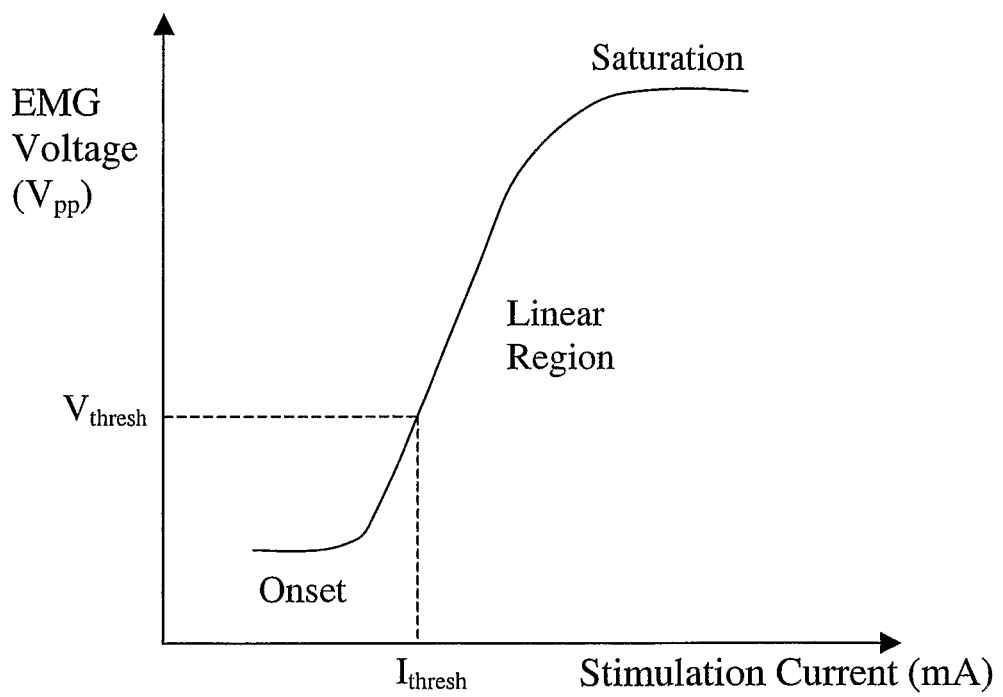
FIG. 7 is a graph illustrating a plot of peak-to-peak voltage (Vpp) for each given stimulation current level ($I_{Stim}$) forming a stimulation current pulse train according to the present invention (otherwise known as a "recruitment curve")

A basic premise behind the neurophysiology employed for the nerve testing (annulus test) in the present invention is that each nerve has a characteristic threshold current level ($I_{Thresh}$) at which it will depolarize. Below this threshold, current stimulation will not evoke a significant neuromuscular response. Once the stimulation threshold ($I_{Thresh}$) is reached, the evoked response is reproducible and increases with increasing stimulation until saturation is reached as shown in FIG. 7. This is known as a "recruitment curve." In one embodiment, a significant EMG response is defined to have a $V_{pp}$ of approximately 100 uV. The lowest stimulation current that evokes this threshold voltage ($V_{Thresh}$) is called $I_{Thresh}$. $I_{thresh}$ decreases as the degree of electrical communication between a stimulation impulse and a nerve increases (e.g. as the insulating annulus gets thinner and/or gets breached). Thus, monitoring $I_{thresh}$ can provide the surgeon with useful information such as the relative thickness of the remaining annulus in a prepared disc space or the integrity of the remaining annulus.

In order to obtain $I_{thresh}$ and take advantage of the useful information it provides, the peak-to-peak voltage ($V_{pp}$) of each EMG response corresponding a given stimulation current ($I_{Stim}$) must be identified. This is complicated by the existence of stimulation and/or noise artifacts which may create an erroneous $V_{pp}$ measurement of the electrically evoked EMG response. To overcome this challenge, the surgical system 10 of the present invention may employ any number of suitable artifact rejection techniques such as those shown and described in full in the above referenced co-pending and commonly assigned PCT App. Ser. No. PCT/US2004/025550, entitled "System and Methods for Performing Dynamic Pedicle Integrity Assessments," filed on Aug. 5, 2004.

Having measured each $V_{pp}$ EMG response, the $V_{pp}$ information is analyzed relative to the stimulation current in order to determine a relationship between the nerve and the given stimulation element transmitting the stimulation current. More specifically, the present invention determines these relationships (between nerve and the stimulation element) by identifying the minimum stimulation current ($I_{Thresh}$) capable of resulting in a predetermined $V_{pp}$ EMG response. According to the present invention, the determination of $I_{Thresh}$, may be accomplished via any of a variety of suitable algorithms or techniques.

FIGS. 8A-8D illustrate, by way of example only, a threshold-hunting algorithm that employs a series of monopolar electrical stimulations to determine the stimulation current threshold $I_{thresh}$ for each EMG channel in range. The nerve is stimulated using current pulses with amplitude of $I_{stim}$. The muscle groups respond with an evoked potential that has a peak-to-peak voltage of $V_{pp}$. The object of this algorithm is to quickly find $I_{Thresh}$, which once again, is the minimum $I_{Stim}$ that results in a $V_{pp}$ that is greater than a known threshold voltage $V_{thresh}$. The value of $I_{stim}$ is adjusted by a bracketing method as follows. The initial bracket size may be, by way of example only, 11.0 mA and 2.0 mA. If the $V_{pp}$ corresponding to both of these stimulation currents is lower than $V_{thresh}$, then the bracket size is doubled to 2.0 mA and 4.0 mA. This exponential doubling of the bracket size continues until the upper end of the bracket results in a $V_{pp}$ that is above $V_{thresh}$. The size of the brackets is then reduced by a bisection method. A current stimulation value at the midpoint of the bracket is used and if this results in a $V_{pp}$ that is above $V_{thresh}$, then the lower half becomes the new bracket. Likewise, if the midpoint $V_{pp}$ is below $V_{thresh}$ then the upper half becomes the new bracket. This bisection method is used until the bracket size has been reduced to $I_{thresh}$ mA. $I_{Thresh}$ is the value of $I_{stim}$ that is the higher end of the bracket.

The threshold hunting will support three states: bracketing, bisection, and monitoring. A stimulation current bracket is a range of stimulation currents that bracket the stimulation current threshold $I_{Thresh}$. The upper and/or lower boundaries of a bracket may be indeterminate. The width of a bracket is the upper boundary value minus the lower boundary value. If the stimulation current threshold $I_{Thresh}$ of a channel exceeds the maximum stimulation current, that threshold is considered out-of-range. During the bracketing state, threshold hunting will employ the method below to select stimulation currents and identify stimulation current brackets for each EMG channel in range.

The method for finding the minimum stimulation current uses the methods of bracketing and bisection. The "root" is identified for a function that has the value −1 for stimulation currents that do not evoke adequate response; the function has the value +1 for stimulation currents that evoke a response. The root occurs when the function jumps from −1 to +1 as stimulation current is increased: the function never has the value of precisely zero. The root will not be known precisely, but only with some level of accuracy. The root is found by identifying a range that must contain the root. The upper bound of this range is the lowest stimulation current $I_{Thresh}$ where the function returns the value +1 (i.e. the minimum stimulation current that evokes response).

Figure 8A:
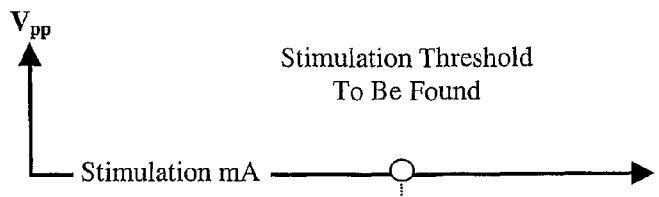
FIG. 8A-8D are graphs illustrating a rapid current threshold-hunting algorithm according to one embodiment of the present invention.
Figure 8B:
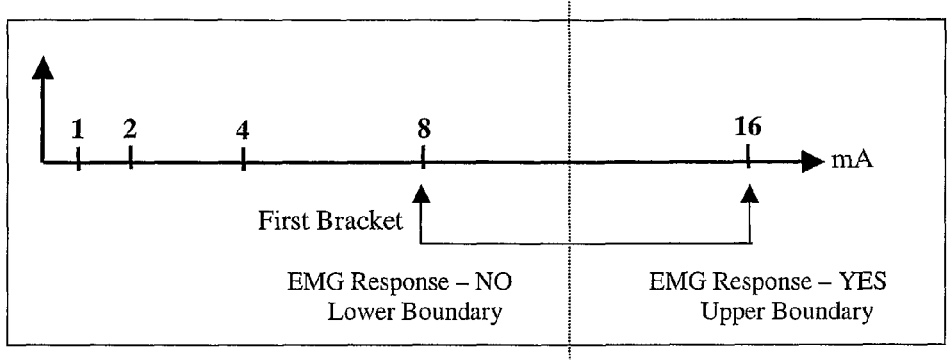
Figure 8C:
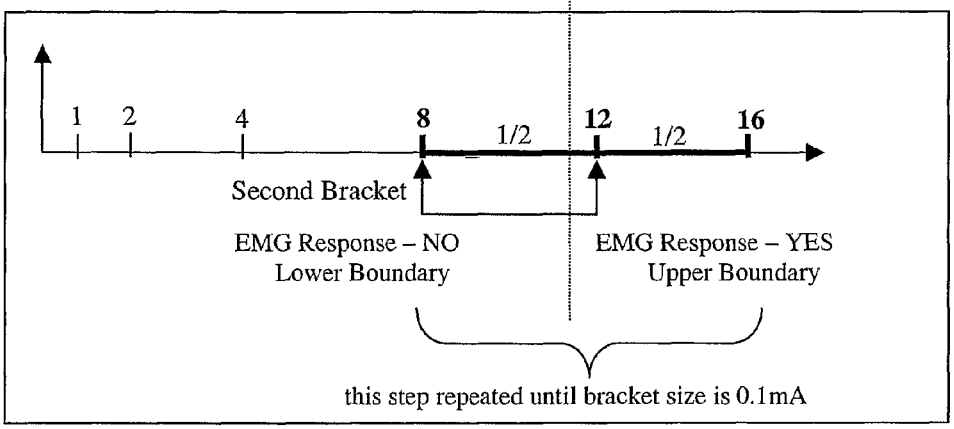
Figure 8D:
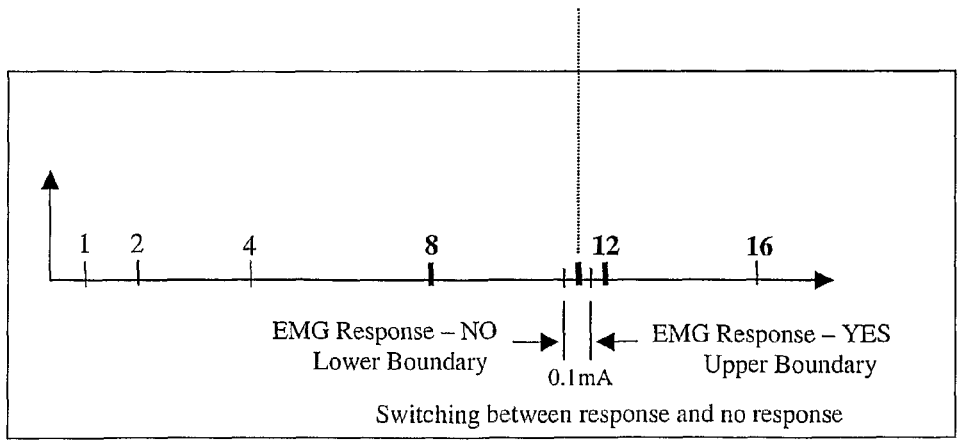

The annulus test function begins by adjusting the stimulation current from on the surgical instrument until the root is bracketed (e.g. "first bracket" in FIG. 8B). The initial bracketing range may be provided in any number of suitable ranges. In one embodiment, the initial bracketing range is 1.0 to 2.0 mA. If the upper stimulation current does not evoke a response, the upper end of the range should be increased. The range scale factor is 2. The stimulation current is preferably never increased by more than 10 mA in one iteration. The stimulation current should never exceed the programmed maximum stimulation current. For each stimulation, the algorithm will examine the response of each active channel to determine whether it falls within that bracket. Once the stimulation current threshold of each channel has been bracketed, the algorithm transitions to the bisection state.

During the bisection state (FIG. 8C), threshold hunting will employ the method described below to select stimulation currents and narrow the bracket to a width of 0.1 mA for each channel with an in-range threshold. After the minimum stimulation current has been bracketed (FIG. 8B), the range containing the root is refined until the root is known with a specified accuracy. The bisection method is used to refine the range containing the root. In one embodiment, the root should be found to a precision of 0.1 mA. During the bisection method, the stimulation current at the midpoint of the bracket is used. If the stimulation evokes a response, the bracket shrinks to the lower half of the previous range. If the stimulation fails to evoke a response, the bracket shrinks to the upper half of the previous range. The algorithm is locked on the electrode position when the response threshold is bracketed by stimulation currents separated by 0.1 mA. The process is repeated for each of the active channels until all thresholds are precisely known. At that time, the algorithm enters the monitoring state.

During the monitoring state (FIG. 8D), threshold hunting will employ the method described below to select stimulation currents and identify whether stimulation current thresholds are changing. In the monitoring state, the stimulation current level is decremented or incremented by 0.1 mA, depending on the response of a specific channel. If the threshold has not changed then the lower end of the bracket should not evoke a response, while the upper end of the bracket should. If either of these conditions fail, the bracket is adjusted accordingly. The process is repeated for each of the active channels to continue to assure that each threshold is bracketed. If stimulations fail to evoke the expected response three times in a row, then the algorithm transitions back to the bracketing state in order to reestablish the bracket.

When it is necessary to determine the stimulation current thresholds ($I_{thresh}$) for more than one channel, they will be obtained by time-multiplexing the threshold-hunting algorithm as shown in FIG. 9. During the bracketing state, the algorithm will start with a stimulation current bracket of 11.0 mA and increase the size of the bracket exponentially. With each bracket, the algorithm will measure the $V_{pp}$ of all channels to determine which bracket they fall into. After this first pass, the algorithm will know which exponential bracket contains the $I_{thresh}$ for each channel. Next, during the bisection state, the algorithm will start with the lowest exponential bracket that contains an $I_{thresh}$ and bisect it until $I_{thresh}$ is found to within 0.1 mA. If there are more than one $I_{thresh}$ within an exponential bracket, they will be separated out during the bisection process, and the one with the lowest value will be found first. During the monitoring state, the algorithm will monitor the upper and lower boundaries of the brackets for each $I_{thresh}$, starting with the lowest. If the $I_{thresh}$ for one or more channels is not found in its bracket, then the algorithm goes back to the bracketing state to re-establish the bracket for those channels.

The information displayed to the user on the display 28 may include, but is not necessarily limited to, alpha-numeric and/or graphical information regarding, myotome/EMG levels, stimulation levels, threshold results ($I_{thresh}$), user instructions, and the instrument in use. In one embodiment (set forth by way of example only) the display includes the following components as set forth in Table 2:

TABLE 2

| Screen Component | Description |
| --- | --- |
| Spine Image 104 | An image of the human body/skeleton showing the electrode placement on or within the body, with labeled channel number tabs on each side (1-4 on the left and right). Left and right labels will show the patient orientation. The Channel number tabs 118 may be highlighted or colored depending on the specific function being performed and the specific electrodes in use. |
| Display Area 106 | Shows procedure-specific information including stimulation results 108 |
| Myotome 110 & Nerve 112 names | A label to indicate the Myotome name and corresponding Nerve(s) associated with the channel of interest. |
| Color Indication | Enhances stimulation results with a color display of green, yellow, or red corresponding to the relative safety level determined by the system. |
| Function Indicator 114 | Graphics and/or name to indicate the currently active function (e.g. Annulus Test). In an alternate embodiment, Graphics and/or name may also be displayed to indicate the instrument in use 120, such as the annulus test probe or disc space probe |
| Stimulation Bar 116 | A graphical stimulation indicator depicting the present stimulation status (i.e.. on or off and stimulation current level) |
| EMG waveforms | EMG waveforms may be optionally displayed on screen along with the stimulation results. |

Figure 3:
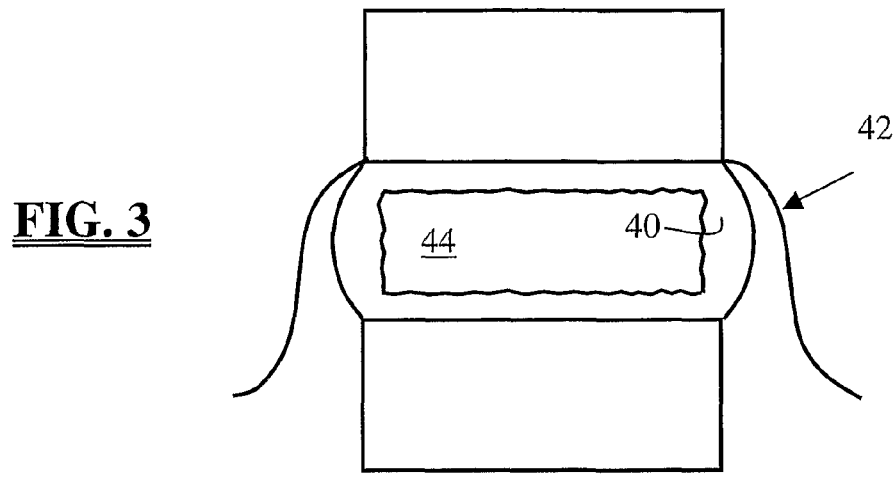
FIG. 3 is a front view of a prepared disc space including a remaining portion of annulus that acts as insulation to adjacent exiting nerve root.

To determine $I_{thresh}$ and assess the adequacy of disc space preparation during and/or after preparation of the disc space, as well as during and/or after introduction of an intradiscal implant, stimulation signals are delivered via one or more of the surgical accessories 24, such as, by way of example only, annulus test probe 32. The annulus test probe 32 includes a handle 34 and a probe member 36 having a generally ball-tipped end 38. The handle 34 may be equipped with one or more buttons for selectively applying the electrical stimulation to the ball-tipped end 38 at the end of the probe member 36. The ball tip 38 of the annulus test probe 32 is placed in contact with the area of interest on the remaining annulus prior to insertion of an intradiscal implant or on the disc implant after insertion. The remaining annulus 40, as illustrated in FIG. 3, will prevent and/or impede the stimulation current (up to a certain amplitude) from communicating with the spinal nerves (not shown) and exiting nerve roots 42. The amount of current amplitude required to communicate with the nerve 42 is at least in part a function of the thickness of the remaining annulus 40 at the stimulation site (e.g. the thicker the annulus is, the higher the current must be to stimulate the nerve). As such, monitoring $I_{thresh}$ may provide valuable information to the surgeon regarding the adequacy of the disc space preparation. By way of example, if the stimulation current required to stimulate the adjacent nerve is high it may indicate that not enough of the disc has been excised in that area. Conversely, if the stimulation current required to stimulate the adjacent nerve is low it may indicate that too much of the disc has been excised or that the remaining annulus has been breached. In use, the ball tipped-end 38 is preferably swept across the posterior aspect (and adjacent lateral sides if desired) of the annulus, or any portion thereof, while dynamically (continuously in real time) detecting $I_{thresh}$. In this way, the thickness of the annulus may be assessed across the entire area of interest and any additional disc preparation may be selectively applied directly to areas in which the annulus remains thick, while thinner areas may be avoided.

Figure 10:
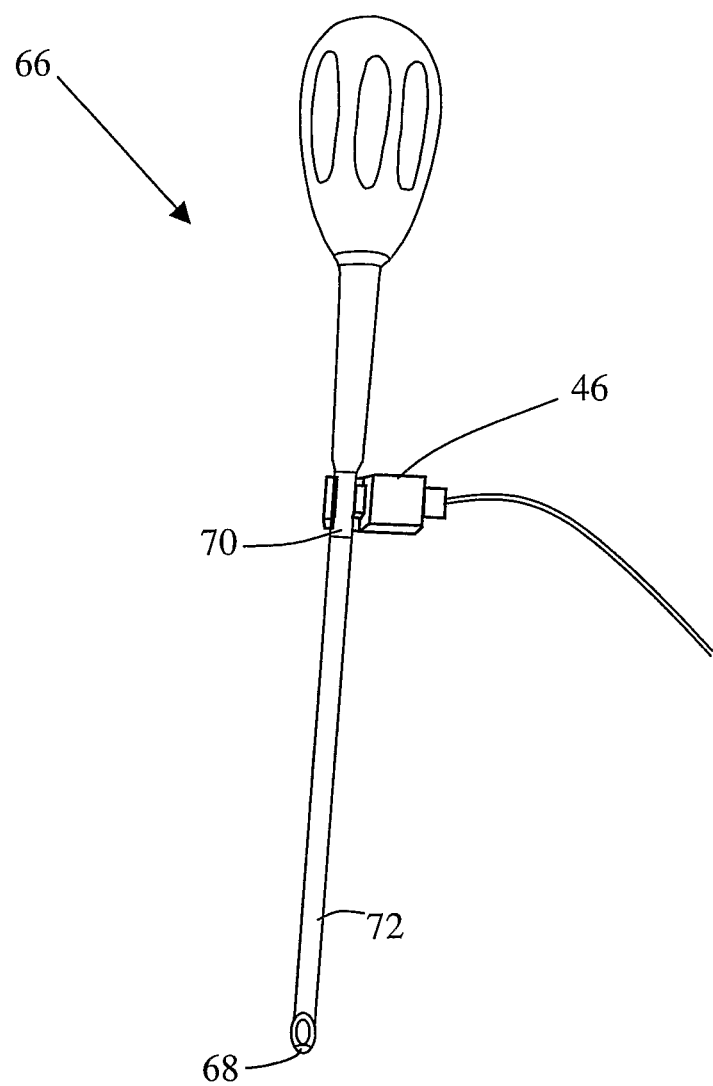
FIG. 10 is an is an illustration of an insulated tool capable of performing dynamic (real time) nerve testing when connected to the system 10.

In one example of an alternate embodiment, the probe member 36 and the ball-tipped end 88 of the annulus probe 32 may be replaced with an electric coupling device. The electric coupling device is utilized to couple a disc space preparation tool, such as for example, a curette 66 (FIG. 10) or pituitary (not shown), to the surgical system 10. Preferably, preparation tools may be configured to include an electrode region 68, for emitting a stimulation signal, and a coupling region 70 for attaching one of the electric coupling devices 47. The remainder of the tool is preferably insulated to ensure the stimulation signal only exits the tool at the electrode region 68. This may be accomplished (by way of example only) by forming the tool from a conductive material, such as metal, and blanketing a significant portion of the tool with an insulating polymeric coating 72, leaving only the electrode region 68 and coupling region 70 uninsulated, as shown in FIG. 4. In this manner, a stimulation signal may be passed through the surgical tool and annulus testing can be performed while the tool is in use. Thus, dynamic testing may be performed during disc space preparation by coupling the surgical tool (e.g. curette or pituitary) to the surgical system 10. Likewise, by coupling an intradiscal implant to the surgical system 10 via the electric coupling device 47, annulus testing may be performed during introduction of the implant.

The electric coupling device may comprise a number of possible embodiments which permit the device to attach and hold a surgical tool while allowing transmission of a stimulation signal to the tool. One such electric coupling device 46 utilizes a spring-loaded plunger to hold the surgical tool and transmit the stimulation signal. The plunger 48 is composed of a conductive material such as metal. A nonconductive housing 50 partially encases the rod 48 about its center. Extending from the housing 50 is an end plate 52. An electrical cable 54 connects the electric coupling device 46 to the handle 34. A spring (not shown) is disposed within the housing 50 such that in a natural or "closed" state the plunger 48 is situated in close proximity to the endplate 52. Exerting a compressive force on the spring (such as by pulling the cable 54 while holding the housing 50) causes a gap between the end plate 52 and the plunger 48 to widen to an "open" position, thereby allowing insertion of a surgical tool between the end plate 52 and plunger 48. Releasing the cable 54 allows the spring to return to a "closed" position, causing the plunger 48 to move laterally back towards the endplate such that a force is exerted upon the surgical tool and thereby holds it in place between the endplate 52 and the plunger 48. Thereafter the electrical stimulus may be passed from the handle 34 through the cable 54 and plunger 48 to the surgical tool.

In an alternate example, the electrical coupling device may be embodied in the form of a clip 56. The clip 56 is comprised of two prongs hingedly coupled at a coupling point 58 such that the clip 56 includes an attachment end 60 and a non-attachment end 62. A stimulation electrode 64 is disposed on the attachment end 60 and communicates with an electric cable 54 extending from the non-attachment end 62 to the handle 34. In a "closed" position the prong ends at the attachment end 60 touch. Depressing the prongs at the non-attachment end 62 in a direction towards each other causes a gap to form between the prong ends at the attachment end 60. Positioning the "opened" attachment end 60 over a desired surgical tool and releasing the force on the non-attachment end 62 causes the attachment end 60 to pinch tight on the surgical tool and thereby allow the electrical stimulus to pass from the annulus probe handle 34, through the stimulation electrode 64, to the surgical tool.

Figure 11:
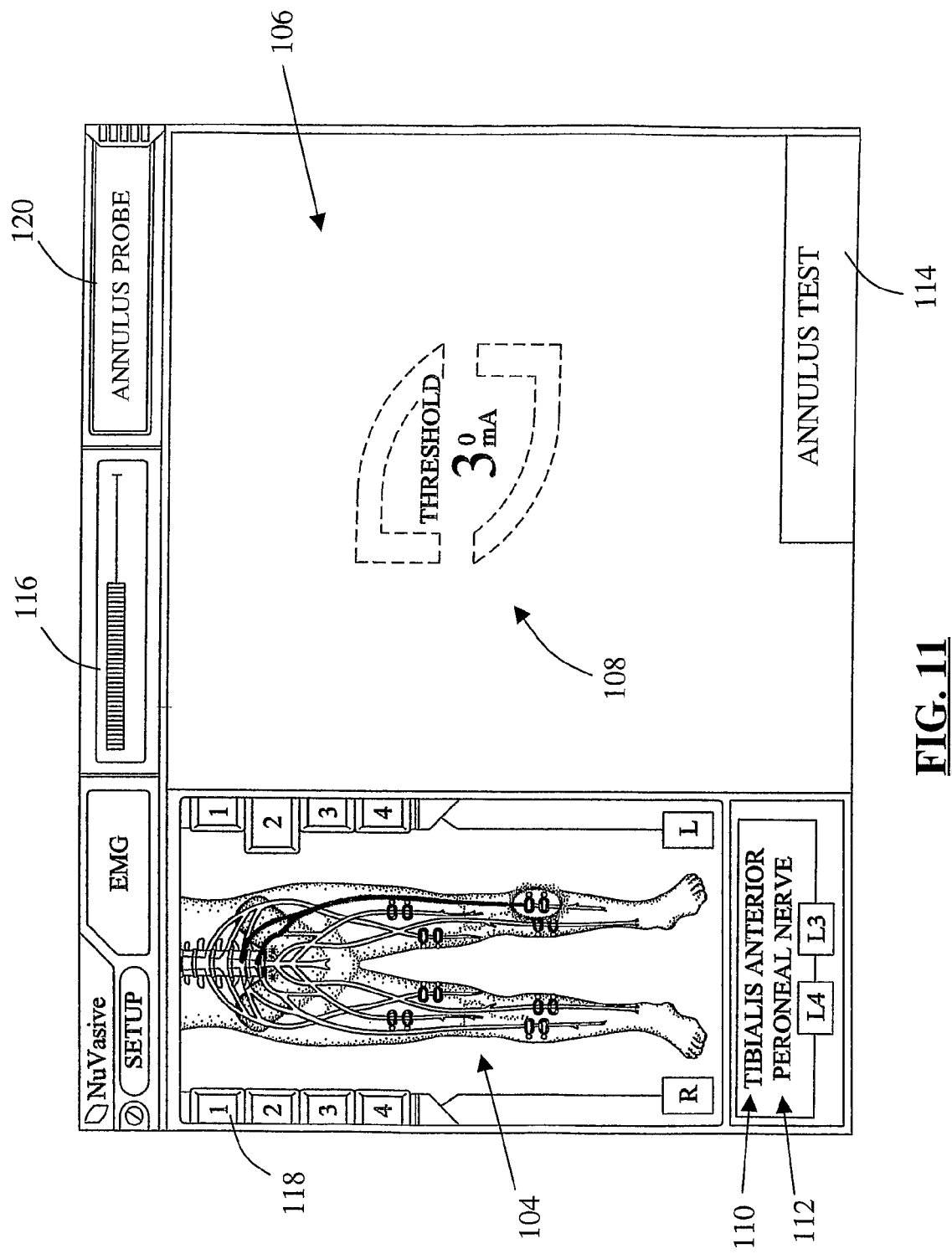
FIG. 11 is an exemplary screen display of one embodiment of the annulus test function performed by the system 10.

FIG. 11 depicts an exemplary screen display of the Annulus Test function using the annulus test probe 32. A function indicator tab 114 indicates that system 10 is set to perform the annulus test and an instrument tab 120 indicates that the annulus test probe 32 is the active instrument. A stimulation bar 116 provides a graphical representation of the stimulation current. Upon pressing the button on the stimulation handle 34, the system 10 determines $I_{thresh}$ for each channel in range. The EMG channel possessing the lowest stimulation result 108 may be automatically highlighted and/or colored to clearly indicate this fact to the user. Additionally, EMG channel tabs 118 may be selected via the touch screen display 28 to show the result 108 of the corresponding nerves. An image of the human body/skeleton 104 shows the electrode placement on or within the body and preferably highlights the electrodes associated with a selected channel. During the annulus test, the system 10 continuously monitors $I_{thresh}$, and the stimulation results 108 shown in the display area 106 are updated after each threshold determination to reflect the lowest threshold detected. The stimulation results may be displayed to the surgeon in conjunction with a color code including colors red, yellow, and green. Red, yellow, and green are preferably displayed to indicate to the surgeon the level of safety determined by the system 10, wherein green represents a safe level, red an unsafe level, and yellow represents a level in-between the safe and unsafe levels.

Figure 12:
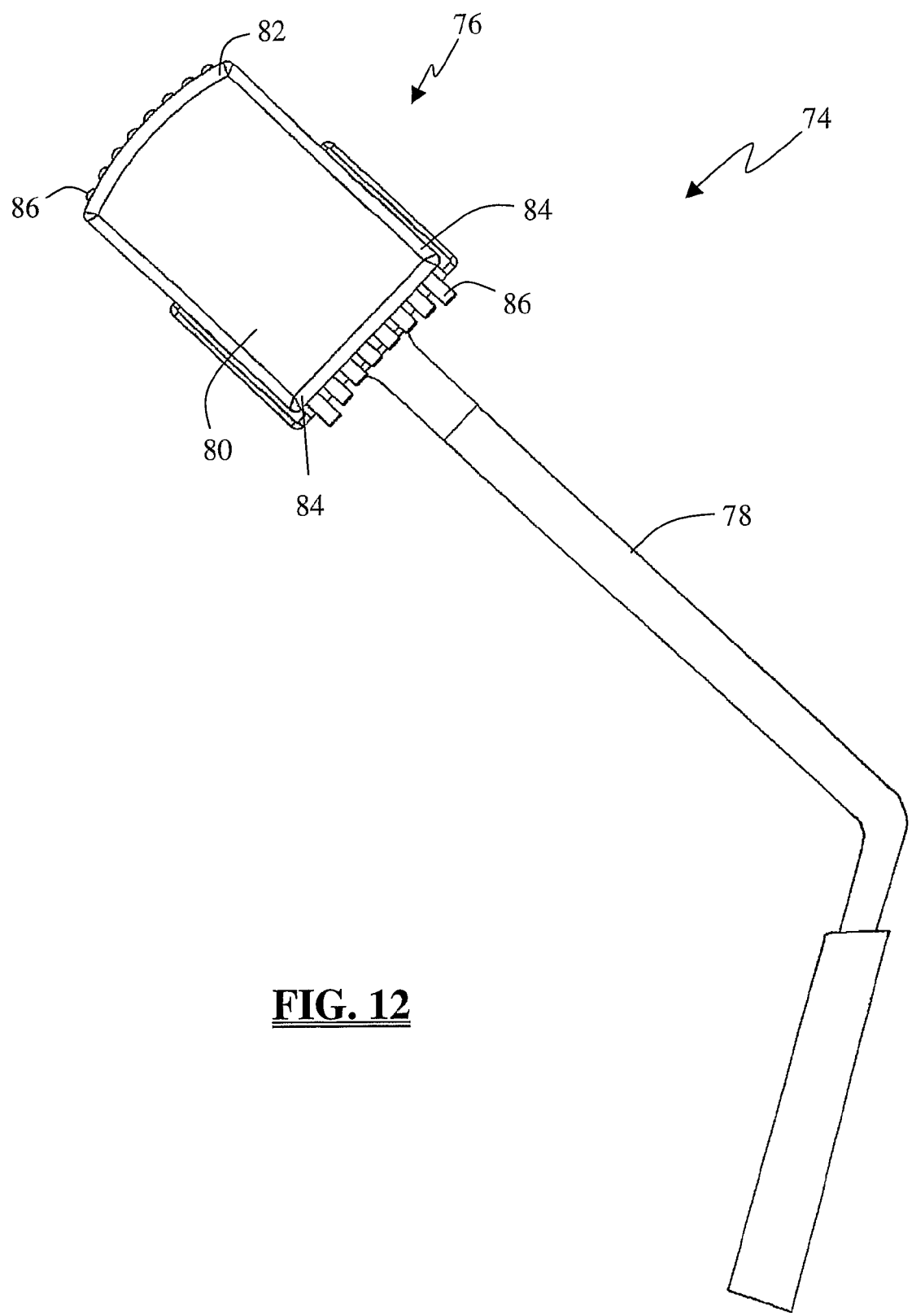
FIG. 12 is a perspective view of an exemplary disc space probe for use with the present invention.
Figure 15:
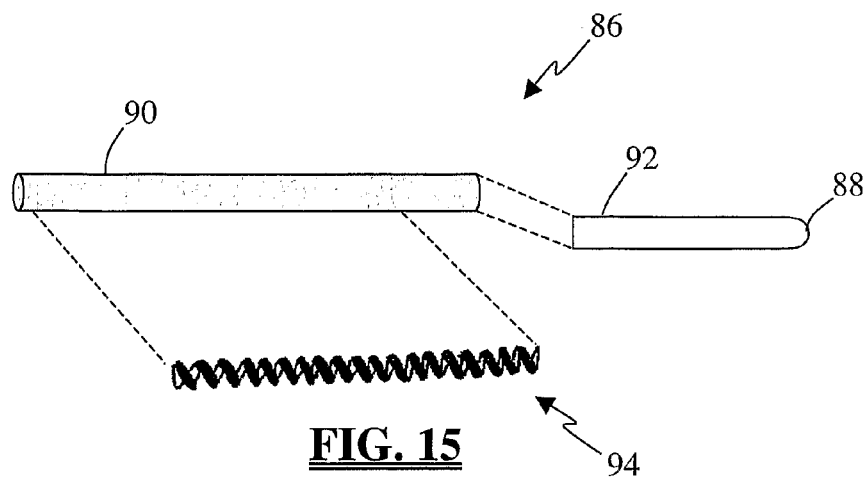
FIGS. 15-16 are exemplary views of pins used in the disc space probe.
Figure 16:
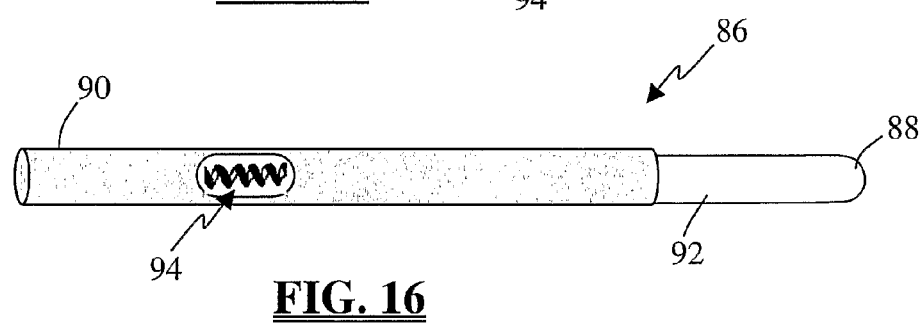
Figure 17:
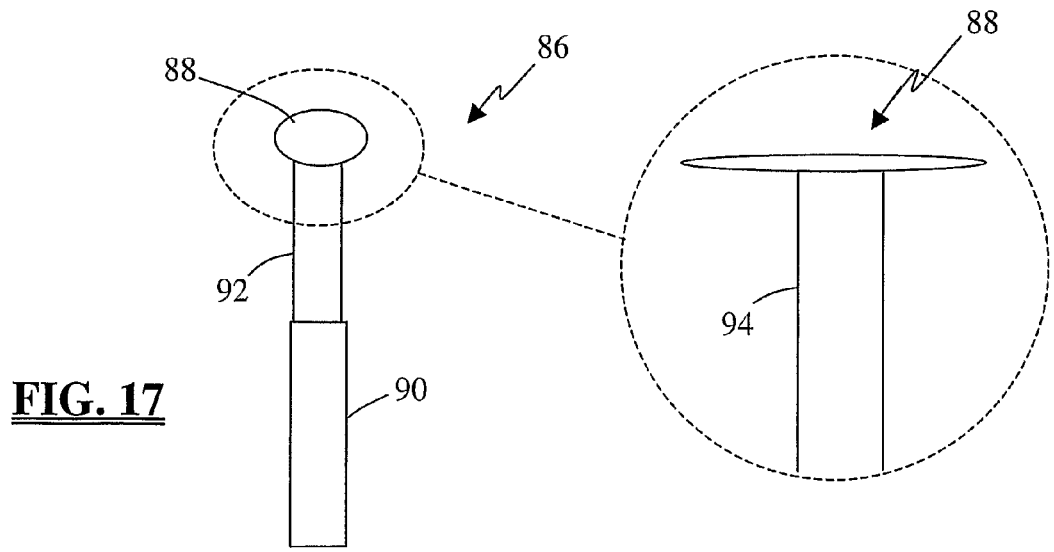
FIG. 17 illustrates an alternate embodiment of the pins used in the disc space probe.

The surgical accessories 24 may further include a disc space probe 74 that may be used in place of, or, in conjunction with annulus test probe 32. With reference to FIGS. 12-13, the disc space probe 74 comprises a probe member 76 and a handle 78. Handle 78 may comprise any instrument suitable for inserting the probe member 76 through an operating corridor into a prepared disc space 44. Probe member 76 includes a nonconductive housing 80, having a distal end 82 and a proximal end 84, and at least two conductive pins 86 extending therethrough. In a preferred embodiment, eight pins 86 composed of a conductive material, such as (for example) metal, extend lengthwise through the interior of the housing 80 protruding for from both distal 82 and proximal 84 ends. Distal end 82 is depicted in FIGS. 12-13 as being fashioned with a generally preferred convex curve which may reduce the risk damaging the annulus or adjacent tissue through inadvertent contact, however, it will be appreciated that distal end 82 may also include a generally concave, or generally flat surface as well. In one example, the heads 88 of pins 86 are generally spherical or rounded, as best viewed in FIGS. 15-16, so as not to damage tissue while entering the disc space or engaging the annulus. Alternatively, pins 86 may have an enlarged, generally circular head 88 with a generally "T-shaped" shaped cross section, as best illustrated in FIG. 17. The "T-shaped" pinheads 88 equally distribute force among the several pins 86, reducing any potential for puncturing the annulus fibrosis. Additionally, the "T-shaped" heads 88 may reduce any potential for the pins to get stuck in small fissures present within the annulus. Preferably, the heads 88 of pins 86 may individually compress in a proximal direction, thus ensuring that each pin 86 may make contact with the annulus despite the different surface curvatures of the disc space and/or any difference in thickness along portions of the annulus. FIGS. 15-16 show, by way of example only, a pin 86 comprising three parts. Pin 86 includes a proximal socket end 90, a distal end 92 ending as head 88, and a spring 94. Spring 94 is contained within socket end 90 and the distal end 92 is inserted into socket end 90 above spring 94. In this manner, when a pin head 88 engages disc tissue before other heads 88, the distal end 92 may compress into the socket end 90 as probe member 74 advances further into the disc space 44, as illustrated in FIG. 14.

Probe member 76 is dimensioned such that it may be positioned within a prepared disc space 44. In one embodiment, distal end 82 of probe member 76 is preferably dimensioned such that it engages a substantial portion of the posterior aspect of the annulus, as best viewed in FIG. 14. This allows the position of probe 74 within the disc space 44 to be approximated with relative accuracy and the $I_{thresh}$ determined for each pin 86 may be associated and displayed with respect to a particular site or region of the annulus. By way of example only, probe member 76 may have a length at its center of approximately 37 mm, a width of approximately 27.5 mm, and a thickness of approximately 9 mm. In other embodiments, probe member 76 may have smaller dimensions, allowing distal end 82 to mate with different surface curvatures of the disc space 44, as best demonstrated in FIGS. 14, 22, 24. The $I_{thresh}$ results may be displayed relative to their position on probe member 76 rather than their position on the annulus and/or various methods (described below) may be employed allowing the system 10 to determine the position of the probe within the annulus.

In use disc space probe 74 is inserted into a prepared disc space 44, such as that illustrated in FIGS. 3 and 14. Distal end 82 is positioned within the disc space such that the heads 88 of pins 86 engage the remaining annulus 40, which again serves to insulate the adjacent spinal nerves and exiting nerve roots 42 from inadvertent contact with a surgical tool or implant. Stimulation impulses are applied one at a time to each pin 86 and the stimulation threshold, $I_{thresh}$, required to evoke a significant EMG response from the muscles innervated by the adjacent nerves is calculated for each pin 86. The individual stimulation thresholds determined provide an indication of annular thickness at each pin position. Using this information, the surgeon may selectively excise more tissue from thicker areas of the annulus and avoid excising additional tissue from thinner areas. The surgeon is thereby able to achieve the advantageous result of removing more annular tissue without increasing the risk to adjacent nerves.

In one embodiment, stimulation impulses may be applied manually to each pin 86, one by one. By way of example only, annulus test probe 32 may be used to apply a stimulation signal to each pin 86 (as depicted in FIG. 14). The ball tipped end 38 of annulus test probe 32 may engage the proximal end 90 of pins 86. To facilitate engagement, the proximal end 90 of pins 86 may be generally convex or cup shaped such that it may easily receive the ball tipped end 38. Upon engagement of each pin 86 and annulus test probe 32, a button on the annulus test probe handle 34 may be pressed initiating a series of stimulation signals by which the stimulation threshold, $I_{thresh}$, may be determined.

Figure 18:
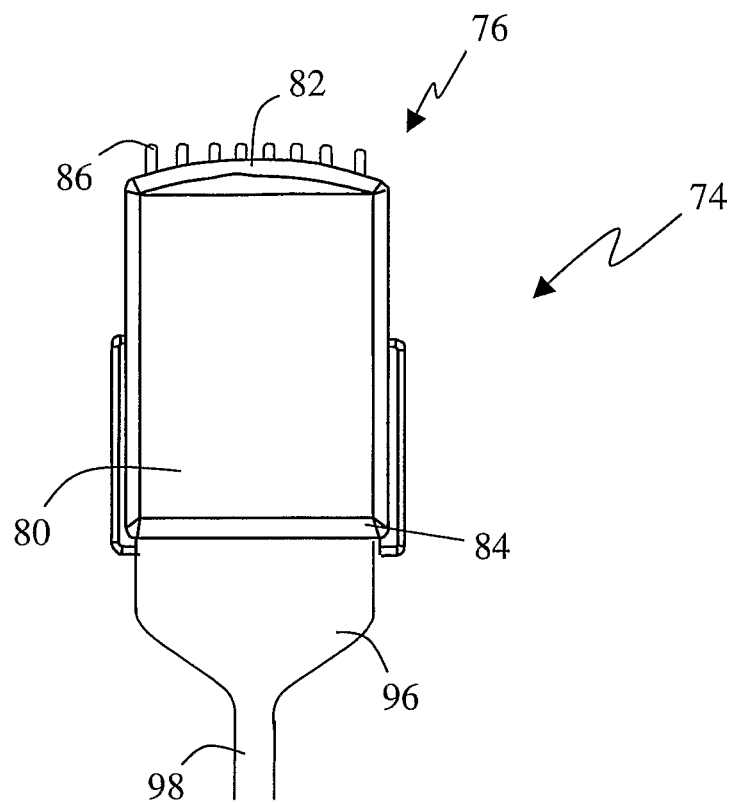
FIG. 18 is a top view of the probe member of FIG. 12 with an electrical connector for communicating with the control unit attached.
Figure 19:
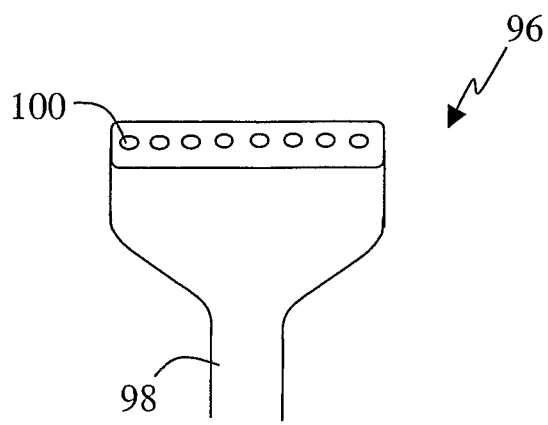
FIG. 19 is a perspective view of the electrical connector of FIG. 18.

In an alternate embodiment, the surgical system 10 may automatically apply stimulation to each pin 86, one by one. Shown by way of example only in FIG. 18-19, a female connecter 96 provided with socket holes 100 for engaging the tail end of all pins 86. Connector 96 is communicatively linked to the surgical system 10 via cable 98. Preferably, connector 96 is attached to handle 34, replacing probe member 36 and ball tipped end 38. Upon pressing the button on handle 34, the system 10 automatically delivers a series of stimulation impulses one at a time to each pin 86 until the stimulation threshold is found for each in turn. Alternatively, pressing the button on handle 34 may stimulate only one pin 86. After completion of each threshold determination, the system 10 automatically switches to the next pin 86 in sequence and pressing the button on handle 34 again will initiates the threshold determination for that pin 86.

Figure 20:
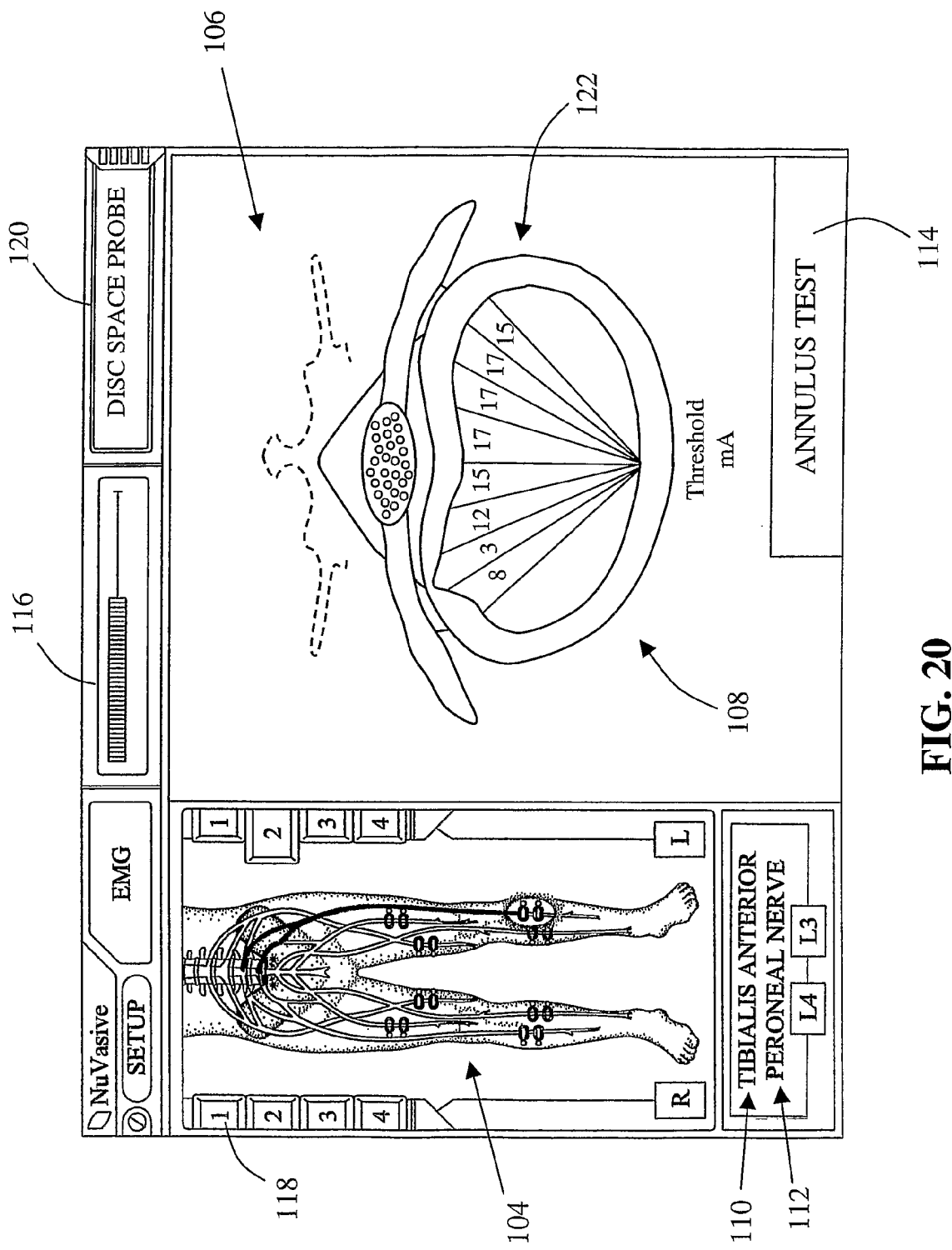
FIG. 20 an exemplary screen display of another embodiment of the annulus test function performed by the system 10.
Figure 21:
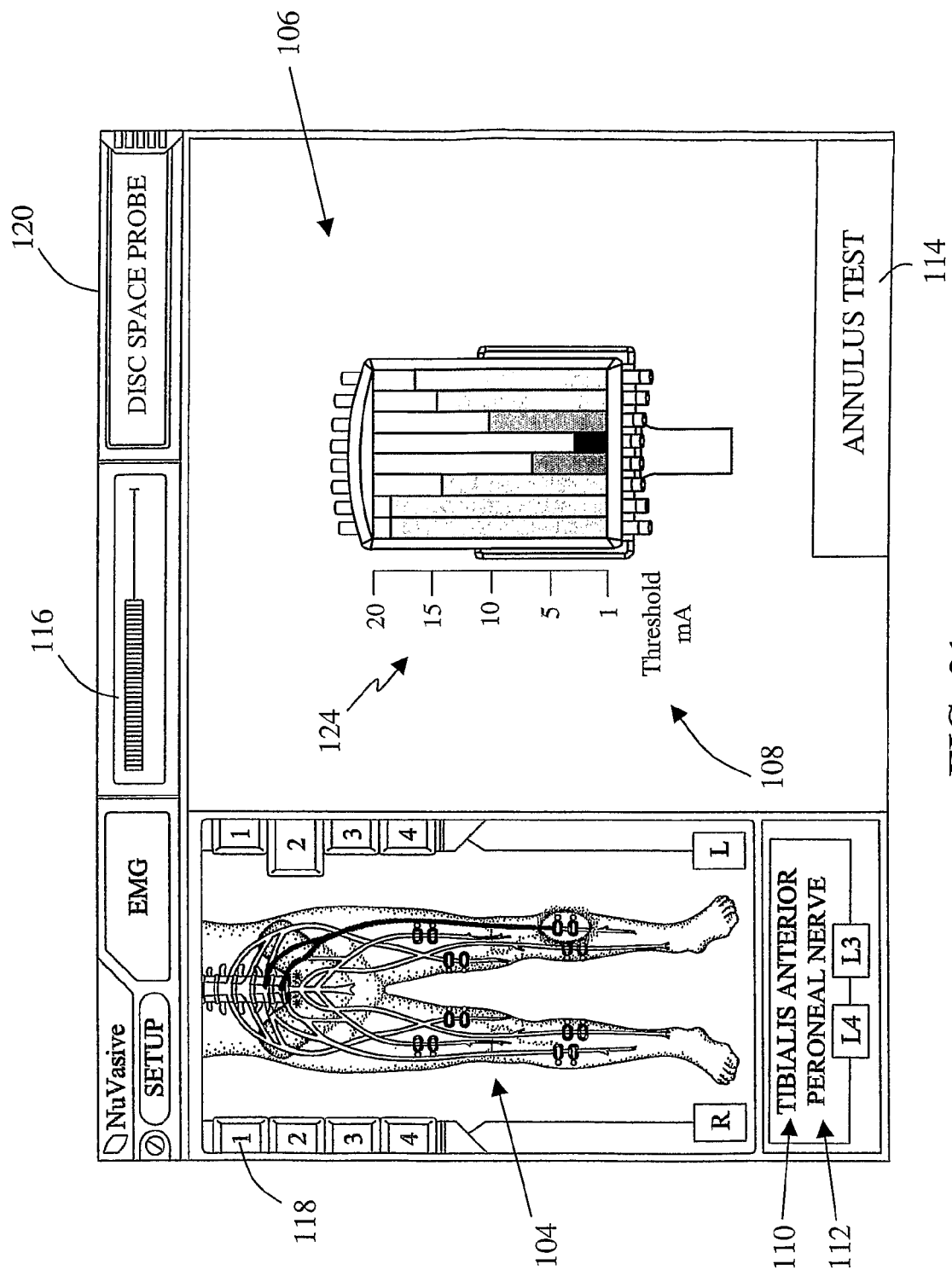
FIG. 21 an exemplary screen display of yet another embodiment of the annulus test function performed by the system 10.

FIGS. 20-21 are exemplary screen displays, set forth by way of example only, of alternate embodiments of the annulus test function. FIG. 20 represents a preferred embodiment of the annulus test function when the position of the probe member 76 within the disc space is known by the system 10, such as for example only, when the dimensions of the probe member 76 are substantially similar to the dimensions of the disc. FIG. 21 represents a preferred embodiment of the annulus test function when the position of the probe member 76 within the disc space is not known by the system 10, such as for example only, when the dimensions of the probe member 76 are substantially dissimilar to the dimensions of the disc. On both display embodiments a function indicator tab 114 indicates that system 10 is set to perform the annulus test and an instrument tab 120 indicates that the disc space probe 76 is the active instrument. A stimulation bar 116 provides a graphical representation of the stimulation current. Upon pressing the button on the stimulation handle 34 the system 10 determines I$_{thresh}$ for each channel in range, for each pin 86 in sequence. EMG channel tabs 118 may be selected via the touch screen display 28 to view a specific stimulation result 108. The lowest stimulation threshold determined for each pin 86 is shown in the display area 106 so that the results may be compared to one another and against predetermined parameters.

FIG. 20 includes a 2-dimensional model 122 of a disc space positioned in the display area 106. Stimulation results 108 for each pin 86 are displayed within the model to relate each stimulation threshold to a site or region on the actual annulus. In FIG. 21, stimulation results 108 are displayed as a bar graph 124 and preferably the bar graph is arranged on an enlarged image of the probe member 76 such that each bar on the graph may be visually correlated to a specific pin 86 on the probe member 76. The stimulation results may be displayed to the surgeon in conjunction with a color indicator including the colors red, yellow, and green. Red, yellow, and green are preferably displayed to indicate to the surgeon the level of safety determined by the system 10, wherein green represents a safe level, red represents an unsafe level, and yellow represents a level in-between the safe and unsafe levels. In one embodiment, set forth by way of example only, a green display corresponds to a stimulation threshold range of 10 mA or greater, a yellow display denotes a stimulation threshold range of 5-9 mA, and a red display denotes a stimulation threshold range of 4 mA or below.

Figure 22:
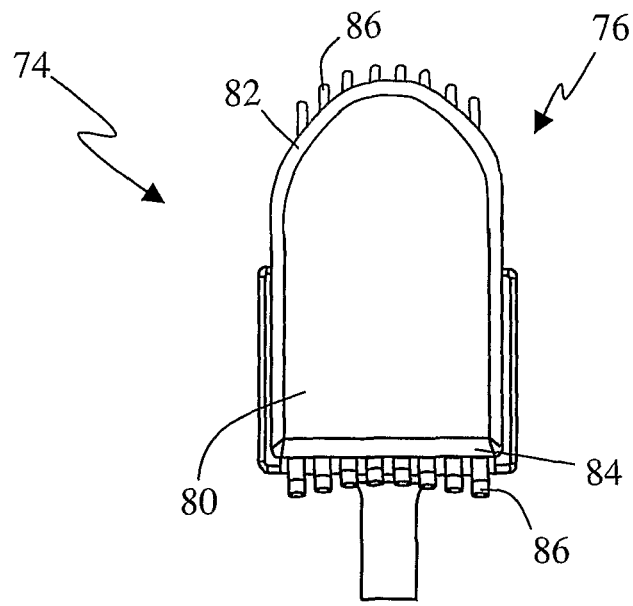
FIG. 22 is a top view of a second embodiment of the disc space probe of FIG. 12 where the distal end is rounded.
Figure 23:
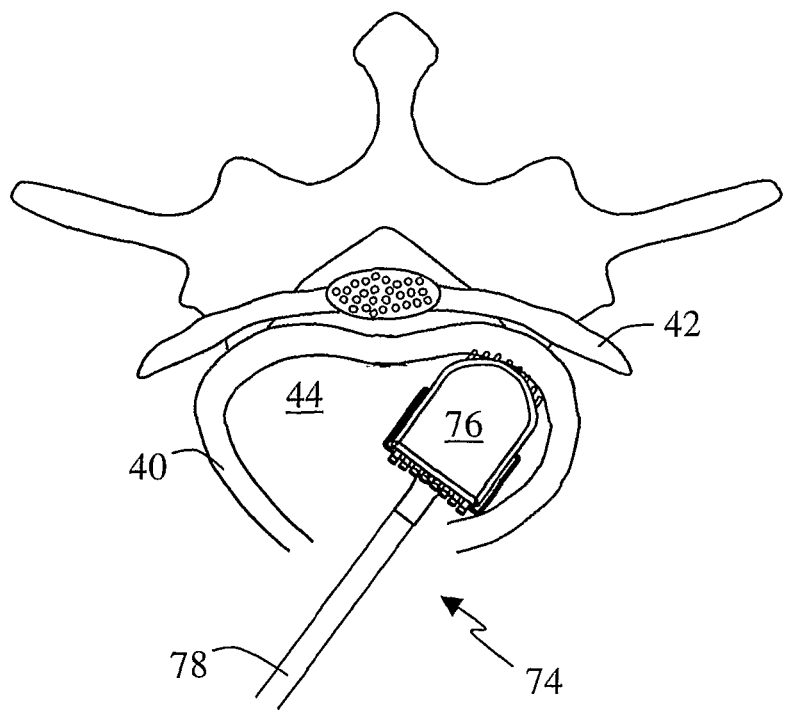
FIG. 23 is a top view of the disc space probe of FIG. 21 inserted in a prepared disc space.

FIG. 22 illustrates an example of an alternate embodiment of the present invention. Distal end 82 has a generally rounded shape that contours to the shape of the posteriolateral portion of the annulus which may be desirable when an anteriolateral approach is used as illustrated in FIG. 23. Although not shown, it is contemplated as forming part of the present invention to provide the distal end 82 having a suitable shape and angle with respect to the handle to permit the disc space probes of the present invention to be used in a generally lateral approach.

Figure 24:
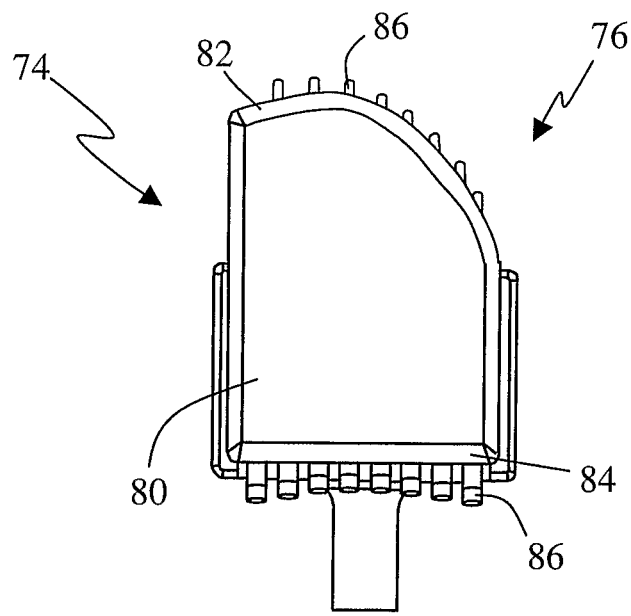
FIG. 24 is a top view of a third embodiment of the disc space probe of FIG. 12 where the distal end has a generally sloped edge.
Figure 25:
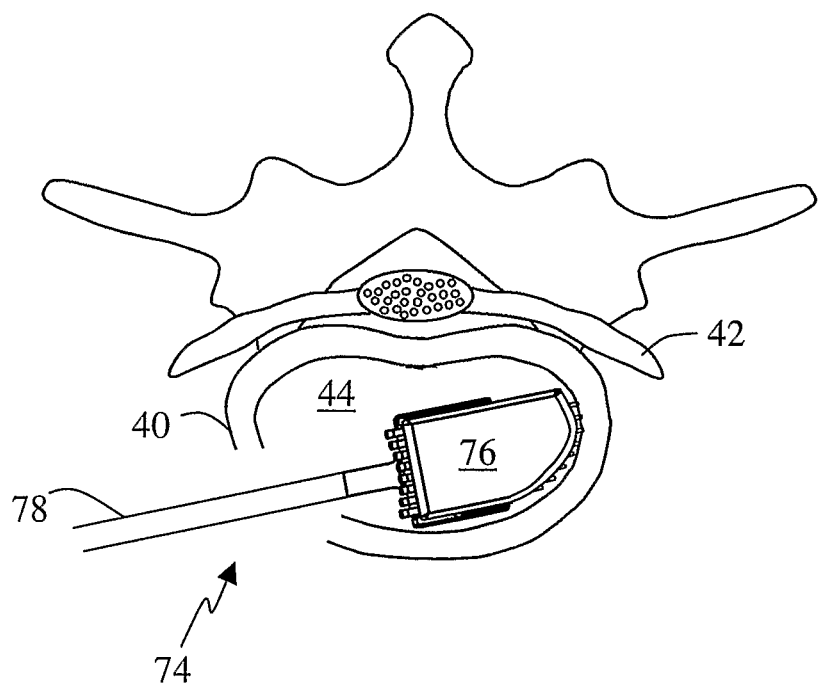
FIG. 25 is a top view of the disc space probe of FIG. 23 inserted in a prepared disc space.

FIG. 24 illustrates still another embodiment of the present invention. Distal end 82 has a generally half rounded shape, maintaining the original convex curve shown in FIG. 13 from one edge to the approximate center and steeply sloping toward the other edge. This shape allows disc test probe 74 to accommodate a more pronounced anteriolateral approach such as that as illustrated in FIG. 25. Although probe member 74 is shown with the distal end 82 sloped in only one direction, it will be appreciated that distal end 82 may be sloped in either direction to accommodate an anteriolateral approach from either side of the body.

FIG. 26A-26C illustrate yet one more embodiment of the present invention. The probe member 76 of the test probe 74 is comprised of modular sections 102 such that one or more sections 102 may be selectively removed depending on the specific needs and requirements of the procedure. This embodiment incorporates all the advantages of the above-described embodiments into a single probe. Removing one or more modular sections 102 decreases the width of the probe 74 allowing the probe to maneuver through small openings and to accommodate different surface curvatures. FIG. 26A shows the modular probe member 76 with no sections 102 removed. FIG. 26B shows the probe member 76 after a section 102 has been removed from one side and FIG. 26C shows the probe member after a section 102 has been removed from the center. Although probe member 76 is shown in FIG. 26A-26C to contain no more than three modular sections 102, it will be appreciated that the probe member 76 may include any suitable number of modular sections 102. FIG. 27A-27B illustrates the probe 74 of FIG. 26A-26C in use with the disc space 44.

Figure 28:
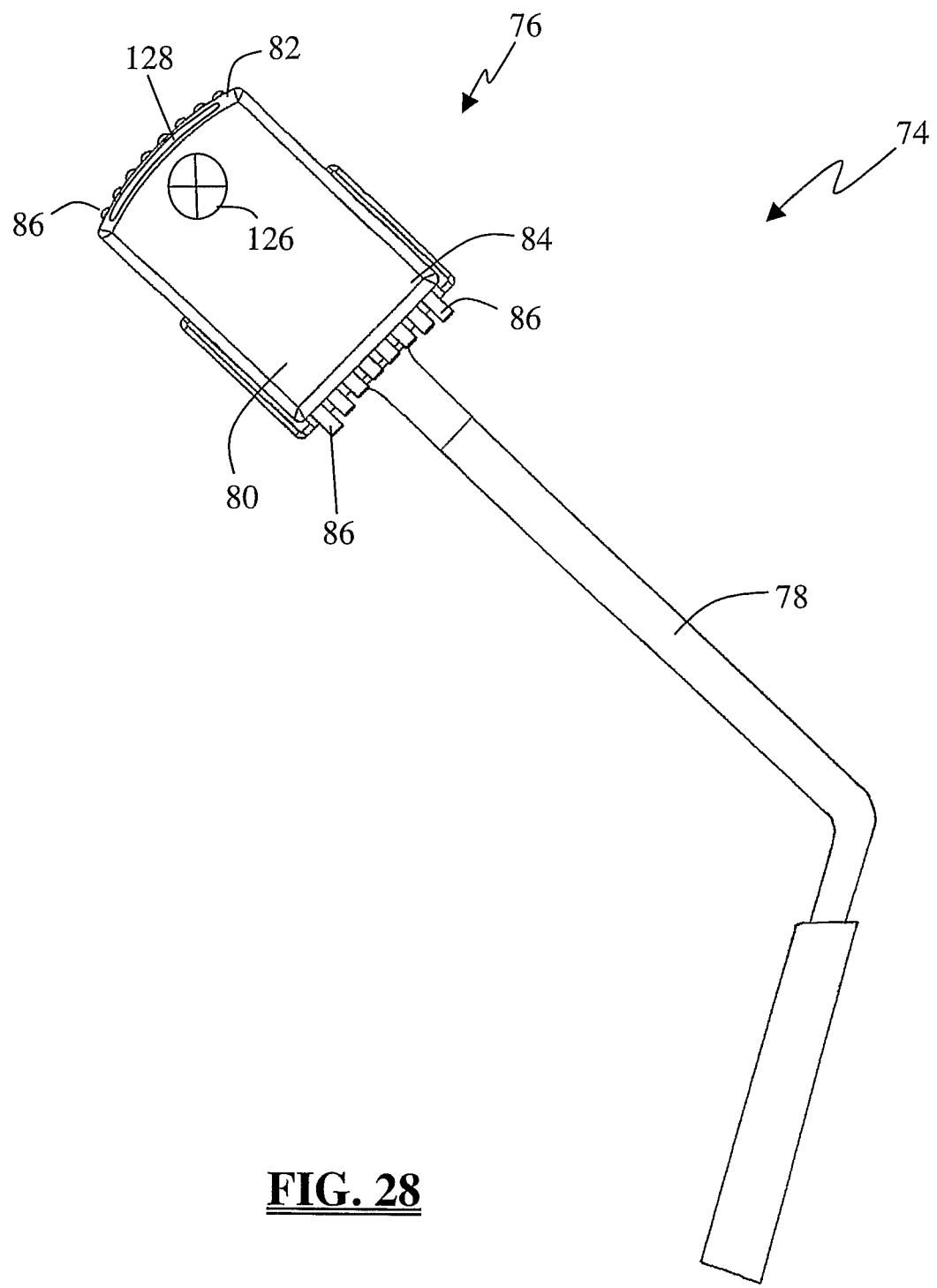
FIG. 28 illustrates a disc space probe equipped with a tracking element for use with a position tracking system to monitor the position of the probe within the disc space.

Any of the various exemplary embodiments of disc space probe 74 and annulus test probe 32 described above may optionally be equipped with tracking elements 126 comprising part of a position tracking system (PTS) operatively linked to the surgical system 10. The PTS may be used to track the position and orientation of the probes 74, 32 while in use within the body. PTSs are believed to be well known in the prior art and will thus be described only briefly below. A variety of different PTSs may be suitable for use with the surgical system 10. In one embodiment, the PTS may be a magnetic tracking system, such as, for the purposes of example only, the miniBIRD™ and microBIRD™ systems offered commercially by Ascension Technology Corporation (Burlington, Vt.). The tracking element 126 in the magnetic tracking system may be a magnetic field sensor that detects and measures magnetic fields emitted by a nearby transmitter fixed in a known position. Alternatively, the tracking element 126 may be a small transmitter that generates a magnetic field, which is detected and measured by a magnetic field sensor fixed in a known position. The tracking element is preferably attached to or integrated in the probe member 76 of disc space probe 74, or, near the ball-tipped end of annulus test probe 32, as depicted in FIG. 28. The position and orientation of the tracking element 126 may be continuously determined relative to the known fixed position of the transmitter or sensor and thus the position of the probes 70, 32 may also be determined. The magnetic tracking system may be configured to automatically disable magnetic field transmission just prior to initiation of a stimulation signal for annulus testing in order to avoid interference between the systems. Magnetic field transmission preferably resumes automatically upon cessation of the stimulation signal.

In second embodiment, the PTS may be an optical tracking system, such as, by way of example only, the OPTOTRACK® and POLARIS® systems offered by Northern Digital Inc. (Ontario, Canada). The tracing elements 126 may include one or more light emitting beacons, such as by way of example only, light-emitting diodes (LED), preferably positioned on the handle members 78, 34 of probes 74, 32, respectively. Alternatively, the tracking elements 126 may include one or more light reflecting beacons that may be detected when illuminated with a light source, such as, for example infrared light. A set of optical sensors or cameras, positioned near the surgical field may be utilized to determine the position and orientation of the tracking elements 126 and thus the position and orientation of the probes 70, 32 may also be determined. Other PTSs, such as for example, global positioning systems and ultrasound tracking systems may also be used.

Figure 29:
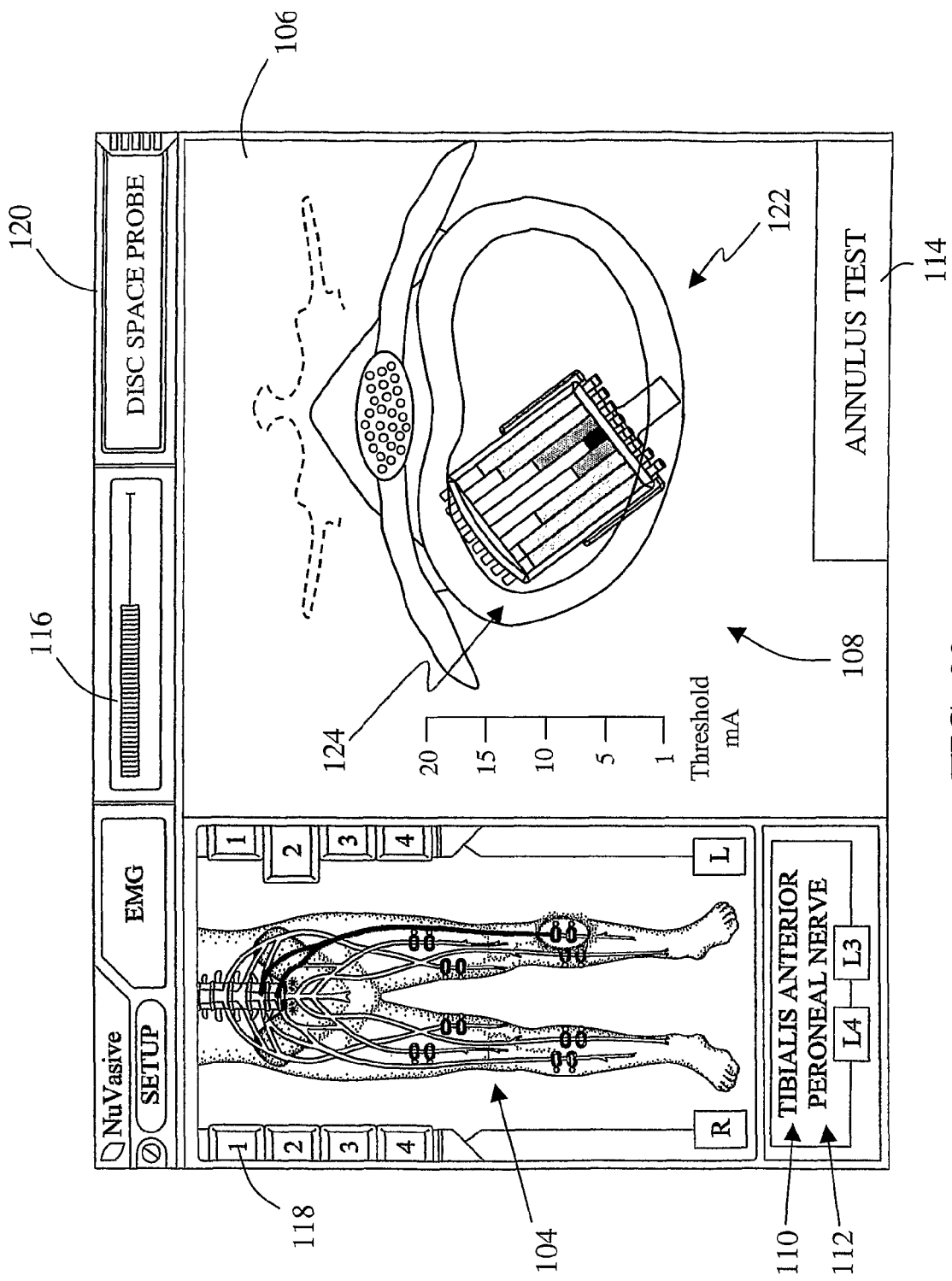
FIG. 29 is an exemplary screen display of another embodiment of the annulus test function wherein the position of the disc space probe within the disc space is shown together with the stimulation results generated by the system 10.

Use of a PTS with the surgical system 10 may further enhance the stimulation threshold information generated by providing positional information to closely relate each $I_{thresh}$ value to a specific site or region within the disc space. This may be accomplished by applying known methods to combine the positional data obtained from tracking element 126 and a disc space image displayed on the GUI 28. With reference to FIG. 29, there is shown a preferred embodiment in which the external image is a 2-dimensional model showing a transverse cross-sectional view of a disc space and adjacent cord and nerve structures. The 2-dimensional model is calibrated to the actual patient disc space such that the position of probes 74, 32 in the actual disc space 44 may be shown with accuracy in the 2-dimensional model. One method of calibration may be performed by tagging exposed or accessible portions of the annulus with at least one, and preferably more, reference markers that are visible to the applicable tracking system. Reference markers may include, by way of example only, additional magnetic field sensors or LEDs depending on the tracking system in use. Corresponding sites on the 2-dimensional model are then identified by user selection on the GUI display and an algorithm is used to register the "patient space" coordinates of the reference markers into the "image space" of the model. Subsequent movement of the tracking elements 126 is tracked relative to the reference markers and the position of probes 74, 32 may thus be shown with accuracy on the 2-dimensional model. In an alternate embodiment the 2-dimensional model 122 may be replaced by actual images of the patients spine obtained prior to or during the surgical procedure such as, such as for example images acquired by MRI, CT, fluoroscopy, among other known imaging techniques. Additional embodiments are contemplated wherein the position of the probes is registered and displayed relative to 3-dimensional images, such as for example, a 3-dimensional model image or 3-dimensional images of the patients own disc space which may be acquired preoperatively.

Figure 30:
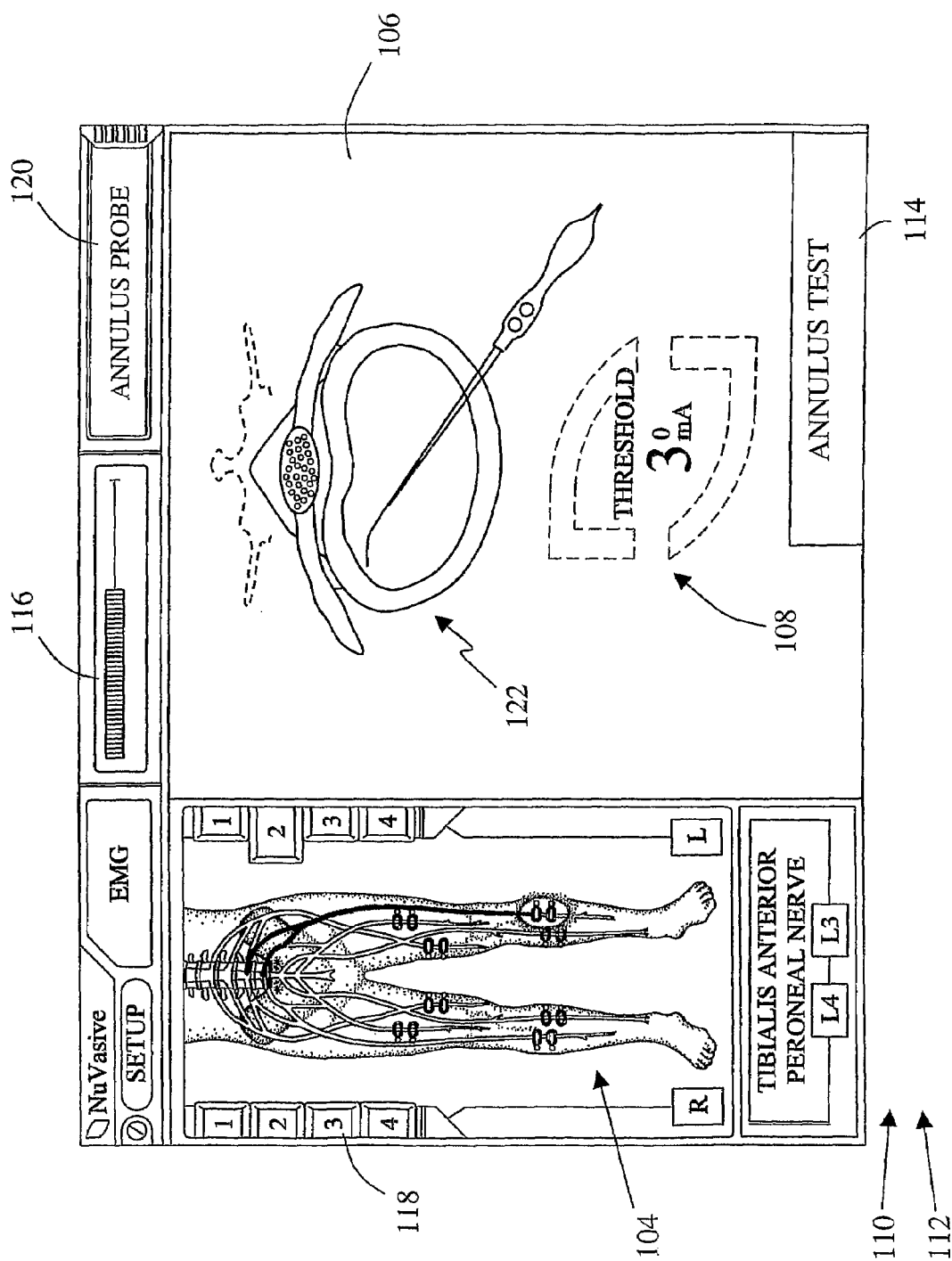
FIG. 30 is an exemplary screen display of another embodiment of the annulus test function wherein the position of the annulus test probe within the disc space is shown together with the stimulation results generated by the system 10.

FIG. 29 illustrates an example of a screen display, set forth by way of example only, for the annulus test function utilizing a PTS to accurately determine the position of the probe within the disc space. A function indicator tab 114 indicates that system 10 is set to perform the annulus test and an instrument tab 120 indicates that the probe in use. A stimulation bar 116 provides a graphical representation of the stimulation current. The lowest stimulation threshold determined for each pin 86 is shown in the display area 106. The display are 106 includes a 2-dimensional model 122 of a disc space. The threshold results 108 are displayed within the disc space model. When disc space probe 74 is used the threshold results are displayed as a bar graph 124 and preferably the bar graph is arranged on an enlarged image of the probe member 76 such that each bar on the graph may be visually correlated to a specific pin 86 on the probe member 76. The stimulation results are positioned to indicate the position of the probe within the disc space 44 as determined by the PTS. When annulus test probe 32 is in use the position of the probe 32 is indicated within the model and the threshold value is displayed separately, as illustrated by way of example only in FIG. 30. Stimulation results are preferably displayed in conjunction with the color indicators as previously described.

To further augment the useful annulus test information provided, the surgical system 10 may be optionally equipped to perform intraoperative ultrasound imaging of the annulus and other adjacent tissues. To do so, the system 10 employs ultrasound equipment and techniques tailored for intraoperative use, which are considered well known in the art and will be described only briefly. At least one ultrasound transducer 128 is preferably attached to or integrated near the distal end of the annulus test probe 32 or disc space probe 74 (FIG. 28). Alternatively, a separate ultrasound probe may be advanced into the disc space alone, or, in conjunction with probes 74 or 32. Under the direction of control unit 12, acoustic signals of a defined frequency, ranging between 50 kHz and 16 MHz, are directed from the transducer towards the annular tissue. The ultrasound signals reflect off tissue boundaries (such as the exterior surface of the annulus) and are received back at the transducer, or at a separate receiving transducer, and then transmitted to the control unit 12 to be converted into viewable images. The ultrasound images graphically represent the annulus and specifically demonstrate the thickness of remaining annulus. The images are preferably shown on the GUI display 28 together with the stimulation threshold data generated by the system 10.

Figure 31:
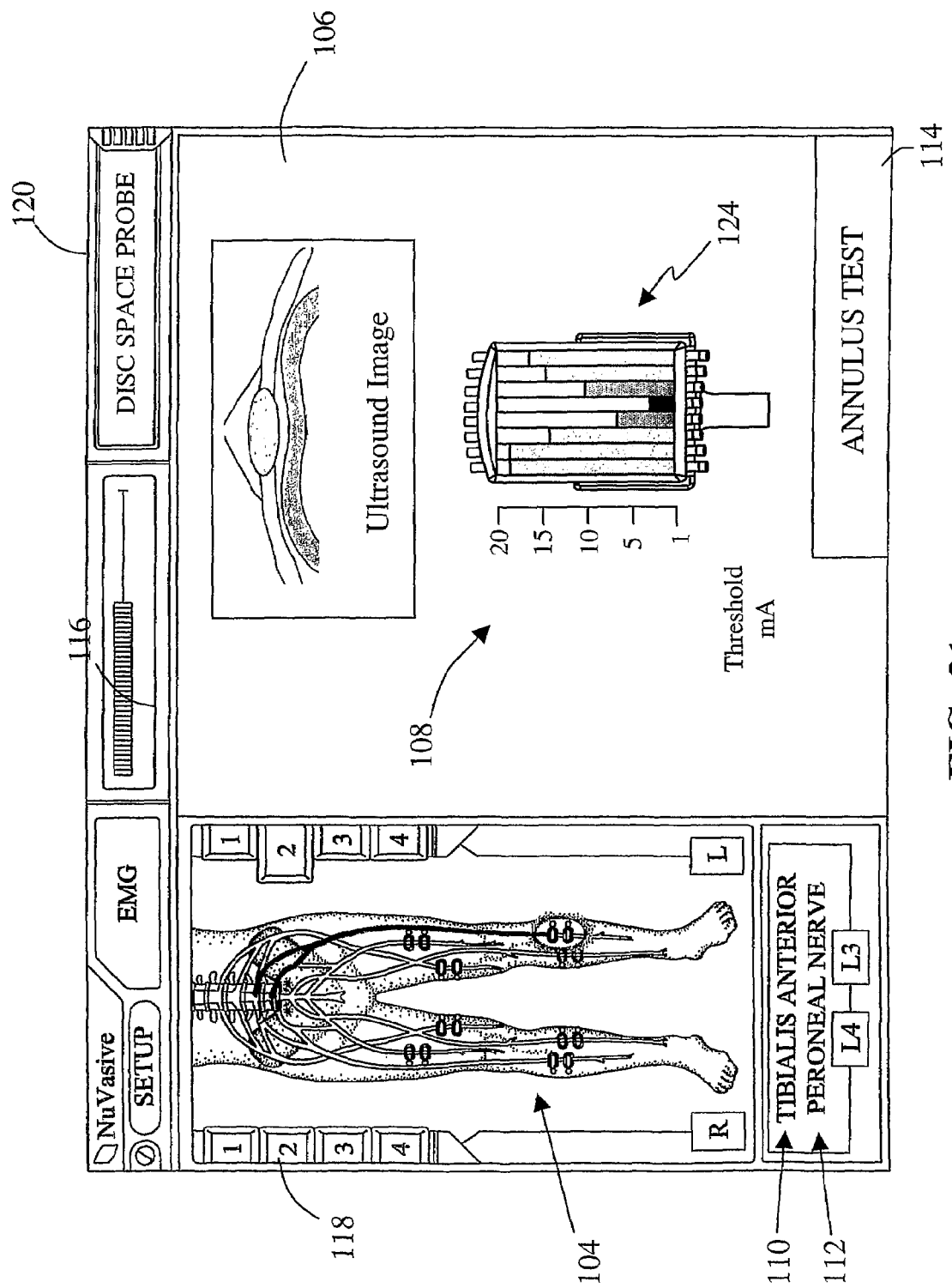
FIG. 31 is an exemplary screen display of another embodiment of the annulus test function wherein an ultrasound image obtained by an annulus test probe or a disc space probe is displayed together with the stimulation results generated by the system 10.

FIG. 31 illustrates one embodiment of a screen display for the annulus test function when ultrasound imaging is utilized. By way of example only, the screen includes the function indicator tab 114, instrument tab 120, stimulation bar 116, channels tabs 118, and spine image 104 described above. Stimulation threshold results are shown in the display area 106 according to any of the methods described above with reference to FIGS. 11, 20, 21. The ultrasound image is shown in the display area 106 together with the stimulation threshold results 108. The annulus may appear as a dark band in the ultrasound image. Preferably, tissue boundaries may be colorized to aid the surgeon in distinguishing the different tissues.

Anterior surgeries, including but not limited to, anterior disc replacement surgery, nucleus replacement, and interbody fusion often require distraction of adjacent vertebral bodies in order to access the disc space and regain proper disc height, as well as compression to ensure the implant remains in the proper position and/or to restore spinal alignment after introduction of an implant. Distracting the vertebral bodies may stretch the nerves, while compression may result in pinching or compression of the exiting nerves, both of which can potentially result in nerve damage or pain. Similarly, insertion of an incorrectly sized intradiscal implant, such as by way of example only, a total disc replacement or interbody fusion cage, may again result in potentially stretching or compressing the exiting nerves and cause nerve damage or pain. In some cases, when a nerve is compressed or stretched, it will emit a burst or train of spontaneous nerve activity. The system 10 may conduct free running EMG to capture this activity. Spontaneous EMG activity may be displayed to the surgeon via the GUI display 28. An audio pick-up may also be provided as an optional feature according to the present invention. The audio pick-up is capable of transmitting sounds representative of such activity such that the surgeon can monitor this response on audio to help him determine if there has been stress to one of the nerves.

The surgical system 10 and related methods have been described above according to one embodiment of the present invention. It will be readily appreciated that various modifications may be undertaken, or certain steps or algorithms omitted or substituted, without departing from the scope of the present invention. For example, the present invention may be implemented using any combination of computer programming software, firmware or hardware. As a preparatory step to practicing the invention or constructing an apparatus according to the invention, the computer programming code (whether software or firmware) according to the invention will typically be stored in one or more machine readable storage mediums such as fixed (hard) drives, diskettes, optical disks, magnetic tape, semiconductor memories such as ROMs, PROMs, etc., thereby making an article of manufacture in accordance with the invention. The article of manufacture containing the computer programming code is used by either executing the code directly from the storage device, by copying the code from the storage device into another storage device such as a hard disk, RAM, etc. or by transmitting the code on a network for remote execution. As can be envisioned by one of skill in the art, many different combinations of the above may be used and accordingly the present invention is not limited by the specified scope. Moreover, although described with reference to the surgical system 10, it will be appreciated as within the scope of the invention to perform nerve testing during anterior surgery, as described herein, with any number of different neurophysiology based testing, including but not limited to the "NIM SPINE" testing system offered by Medtronic Sofamor Danek, Inc.

What is claimed is:

1. A surgical system for assessing disc space preparation during spine surgery, the disc space preparation including excising disc material from an interior of the disc space to make a cavity for receipt of an implant and leaving a layer of annulus tissue to insulate the prepared disc space from neural structures adjacent the annulus tissue, comprising:
    a probe insertable into the cavity of the prepared disc space and configured to transmit a stimulation signal within said disc space to said annulus tissue, wherein said probe includes a handle and a probe member having at least two conductive pins aligned in a nonconductive housing, said conductive pins extending through the nonconductive housing and protruding for a portion from a distal end of the nonconductive housing, the probe member being configured such that the nonconductive pins contact an interior face of the annulus layer when the probe is inserted into the prepared disc space.

2. The surgical system of claim 1, further comprising:
    a sensor configured to detect neuromuscular responses from muscle myotomes associated with said neural structures adjacent the annulus layer; and
    a control unit coupled to said probe and said sensor, said control unit configured to (a) command transmission of said stimulation signal from said probe, (b) receive neuromuscular response data from said sensor, and (c) analyze the neuromuscular response data in relation to the stimulation signal to determine the degree of communication between said probe and said neural structures to assess the disc space preparation.

3. The surgical system of claim 2, wherein said sensor is configured to detect an EMG voltage output of said neuromuscular response and determine a peak-to-peak voltage of said voltage output to characterize said neuromuscular response.

4. The surgical system of claim 3, wherein said control unit determines a threshold stimulation current level necessary to evoke a neuromuscular response characterized by a predetermined peak-to-peak voltage to determine the degree of communication between said probe and said neural structures.

5. The surgical system of claim 2, wherein said control unit is further configured to direct stimulation signals and determine threshold current levels through all of the at least two pins, in sequence.

6. The surgical system of claim 2, further comprising a screen display for displaying at least one of alpha-numeric and graphical information regarding the degree of electrical communication between said probe and said neural structures.

7. The surgical system of claim 6, wherein said alpha-numerical and graphical information includes at least one of a bar graph illustrating threshold stimulation current level determinations, an image of a disc space including threshold stimulation current level determinations arrayed within the disc space image, and a numeral representing a threshold stimulation current level determination.

8. The surgical system of claim 2, further comprising a position tracking system operatively linked to said control unit and a tracking element fixed in a known position on said probe, said position tracking system being configured to register spatial coordinates of reference markers positioned at least one of on and near said annulus tissue, with coordinates of an image representing the disc space and shown on a display, said position tracking system being further configured to continuously determine the coordinate position of said probe relative to said reference markers, said control unit being further configured to display the position of said probe within said image of said disc space together with the results of said stimulation analysis.

9. The surgical system of claim 2, wherein said control unit is further configured to obtain visual images of said annulus tissue and display said images to a user.

10. The surgical system of claim 9, wherein said visual images are ultrasound images.

11. The surgical system of claim 9, wherein said probe includes at least one ultrasound transducer fixed near a distal end of said probe.

12. The surgical system of claim 1, further comprising at least one of an additional stimulation element for manually touching to a portion of one of said at least two pins extending from the proximal end of said probe member and emitting said stimulation signal through said pin, and an electrical connector including socket holes for mating with proximal ends of said at least two pins to automatically apply said stimulation signals to each of said at least two pins in sequence.

13. The surgical system of claim 1, wherein said at least two pins are individually compressible in a proximal direction.

14. The surgical system of claim 1, wherein said probe member is dimensioned such that if may contact a substantial portion of a posterior aspect of said annulus tissue.

15. The surgical system of claim 1, wherein said probe member is dimensioned such that the probe member may contact only a portion of at least one of a posterior, posteriolateral, and lateral aspect of said annulus tissue.

16. The surgical system of claim 1, wherein said probe member has one of a curved, rounded, half-rounded, and sloped distal end for matching different surface contours of said annulus tissue.

17. The surgical system of claim 1, wherein said nonconductive housing comprises at least two modular sections that may be added and removed to adjust the size and shape of said probe member.

* * * * *